United States Patent [19]

Fujikawa et al.

[11] Patent Number: 4,937,324
[45] Date of Patent: Jun. 26, 1990

[54] CHROMATOGRAPHIC PURIFICATION OF HUMAN PROTEINS HAVING ANTICOAGULANT AND ANTI-INFLAMMATORY ACTIVITY

[75] Inventors: Kazuo Fujikawa; Meher H. Irani; Bruce L. A. Carter, all of Seattle, Wash.

[73] Assignees: ZymoGenetics, Inc.; The Board of Regents of the University of Washington, both of Seattle, Wash.

[21] Appl. No.: 152,383

[22] Filed: Feb. 4, 1988

Related U.S. Application Data

[63] Continuation-in-part of Ser. No. 59,355, Jun. 5, 1987, which is a continuation-in-part of Ser. No. 11,782, Feb. 6, 1987.

[51] Int. Cl.$^5$ .......................... C07K 3/02; C07K 3/22; C07K 3/24; C07K 15/06
[52] U.S. Cl. ..................................... 530/397; 530/412; 530/416; 530/417; 530/420; 530/350; 530/851
[58] Field of Search ............... 530/395, 412, 414, 415, 530/416, 417, 420, 419

[56] References Cited

U.S. PATENT DOCUMENTS

| | | | |
|---|---|---|---|
| 4,191,533 | 3/1980 | Bohn et al. | 530/851 |
| 4,217,339 | 8/1980 | Bohn et al. | 429/105 |
| 4,348,316 | 9/1982 | Bohn | 530/851 |
| 4,402,872 | 9/1983 | Bohn | 530/851 |
| 4,500,951 | 2/1985 | Bohn et al. | 530/415 |
| 4,592,863 | 6/1986 | Bohn et al. | 530/350 |
| 4,594,328 | 6/1986 | Bohn et al. | 530/395 |
| 4,732,891 | 3/1988 | Maki et al. | 530/851 |
| 4,736,018 | 4/1988 | Reutelingsperger | 530/381 |
| 4,746,731 | 5/1988 | Bohn et al. | 530/394 |

OTHER PUBLICATIONS

Clark et al., Chapter II, in "Experimental Biochemistry", pp. 15–28 (1971).
Wallner et al., Nature, 300, 77–81, (Mar. 6, 1986).
Reutlinsperger et al., Eur. J. Bioch., 151, 625–629 (1985).
Valentine-Braun et al. *PNAS* 83:236–240, 1986.
Warn-Cramer et al., *Circulation* 74:11-408, 1986.
Broze and Milletich, *Circulation* 74:11-409, 1986.
Huang et al., *Cell* 46:191–199, 1986.
Nelsestuen and Broderius, *Biochemistry* 16:4172–4177, 1977.
Pepinsky et al. *J. Biol. Chem.* 261:4239–4246, 1986.
Flower, *Agents and Actions* 17:255–262, 1985.
Wallner et al. *Nature* 320:77–81, 1986.
Geisow and Walker *TIBS* 11:420–423, 1986.
Kretsinger and Creutz, *Nature* 320:573, 1986.
Iwasaki et al. *J. Biochem.* 102:1261–1273, 1987.
Flower, *Nature* 320:20, 1986.
Schlaepfer et al. *PNAS* 84:6078–6082, 1987.
Deykin et al. *Biochem. Biophys. Res. Comm.* 34:245–251, 1969.
Deykin et al. *Circulation* 37/38:VI-5, 1968.
Geisow et al., *Nature* 320:636–638, 1986.
Davidson et al., *J. Biol. Chem.* 262:1698–1705, 1987.
Glenney et al. *J. Cell Biol.* 104:503–511, 1987.
Funakoshi et al., *Biochemistry* 26:5572–5578, 1987.
Funakoshi et al., *Biochemistry* 26:8087–8092, 1987.

Primary Examiner—Margaret Moskowitz
Assistant Examiner—Jeff Kushan
Attorney, Agent, or Firm—Seed and Berry

[57] ABSTRACT

Proteins having therapeutic potential as both anticoagulants and as anti-inflammatory agents are disclosed. The present invention also discloses the use of lipocortins in reducing blood coagulation in warm-blooded animals.

3 Claims, 11 Drawing Sheets

Mono S Column Chromatography of PAP-I

```
              10                20                30                40                50                60
Lipocortin-I  MAMVSEFLKQAWFIENEEQEYVQTVKSSKGGPGSAVSPYPTFNPSSDVAALHKAIMVKGV
PAP-I                                       Ac AQVLRGTVTDFPGFDERADAETLRKAMKGLGT
PAP-II
PAP-III                     PMFXVNTNVPRASVPDGFLLELTQQLAQATGXPPQYXAXGmKGLGT
PAP-IV                      SLEGDHSTPPSAYGSVKAYTNFDAERDALN 70                80                90               100               110               120
Lipocortin-I  DEATIIDILTKRNNAQRQQIKAAYLQETGKPLDETLKKALTGHLEEVVLALKTPAQFDA
PAP-I         DEESILTLLTSRSNAQRQEIIAAFKTLFGRDLLDDLKSELTGKFEKLIVALMKPSRLYDA
PAP-II        DEDAIISVLAYRINTAQRQEIRTAYXSTXGXDLXDDLXSELXGN
PAP-III            mLISILTERSNAQRQLIIVKEYQAAYGKELKDDLKGDLSGH        mVALV
PAP-IV 130               140               150               160               170               180
Lipocortin-I  DELRAAMKGLGTDEDTLIEILASRTNKEIRDINRVYREELKRDLAKDITSGDFRNAL
PAP-I         YELKHALKGAGTNEKVLTEIIASRTPEELRAIKQVVEEEYGSSLEDDVGDTSGYYQRML
PAP-II             mKGAGTDEGCLIIEILASRTPEELRRISQTYQQYGRSLEDDXRSDT
PAP-III            mKGAGINEDALIEILTT           mKDIXQAIIYTVYKKSLGDISGETSGDFRKAL
PAP-IV 190               200               210               220               230               240
Lipocortin-I  LSLAKGDRSEDFGVNEDLADSDARALYEAGERRKGTDVNVFNTILTTRSYPQLRRVFQKY
PAP-I         VVLLQANRDPDAGIDEAQVEQDAQALFQAGELKWGTDEEKFITIFGTRSVSHLRKVFDKY
PAP-II        LVLA
PAP-III
PAP-IV 250               260               270               280               290               300
Lipocortin-I  TKYSKHDMNKNLDLELKGDIEKCLTAIVKCATSKPAFFAEKLHQAMKGVGTRHKALIRIM
PAP-I         MTISGFQIEETIDRETSGNLEQLLLAVVKSIRSIPAYLAETLYYAMKGAGTDDHTLIRVM
PAP-II                              mRNKSAYFAEKLYK   mKGLGTDXN
PAP-III
PAP-IV 310               320               330               340
Lipocortin-I  VSRSEIDMNDIKAFYQKMYGISLCQAILDETKGDYEKILVALCGGN
PAP-I         VSRSEIDLFNIRKEFRKNFATSLYSMIKGDTSGDYKKALLLCGEDD
PAP-II             mLDIRAHFKRLYGKSLYSFIIKGDTSGDYR
PAP-III       VSRSEIDLLDIRTEFKKRYGYSLYSAIIKSDTSGDYEITLLKICGGDD
PAP-IV             mLKIIRSEFKRKYGKSLYYYIIQQ
```

CHROMATOGRAPHIC PURIFICATION OF HUMAN PROTEINS HAVING ANTICOAGULANT AND ANTI-INFLAMMATORY ACTIVITY

CROSS-REFERENCE TO RELATED APPLICATION

This application is a continuation-in-part of U.S. Ser. No. 059,355, filed June 5, 1987, which application is pending and is a continuation-in-part of U.S. Ser. No. 011,782, filed Feb. 6, 1987, which application is pending.

TECHNICAL FIELD

The present invention relates to the production and use of proteins in general, and more specifically, to the production of novel proteins exhibiting anticoagulant and anti-inflammatory activity, DNA sequences encoding these proteins, and the use of these proteins in warmblooded animals.

BACKGROUND OF THE INVENTION

Blood coagulation is a process consisting of a complex interaction of various blood components or factors which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors which have undergone such a conversion are generally referred to as "active factors," and are designated by the addition of a lower case postscript "a" (e.g., factor VIIa).

There are two separate systems which promote blood clotting and which thereby participate in normal hemostasis. These systems have been referred to as the "intrinsic" and the "extrinsic coagulation pathways." The "intrinsic pathway" refers to those reactions which lead to thrombin formation through utilization of factors present only in plasma. An intermediate event in the intrinsic pathway is the activation of factor IX to factor IXa, a reaction catalyzed by factor XIa and calcium ions. Factor IXa then participates in the activation of factor X in the presence of factor VIIIa, phospholipid, and calcium ions.

The "extrinsic pathway" involves plasma factors, and additionally involves components present in tissue extracts. Factor VII, one of the proenzymes referred to above, participates in the extrinsic pathway of blood coagulation by converting (upon its activation to VIIa) factor X to Xa in the presence of tissue factor and calcium ions. Factor Xa in turn converts prothrombin to thrombin in the presence of factor Va, calcium ions, and phospholipid.

In some instances, for example, kidney dialysis, deep vein thrombosis, and disseminated intravascular coagulation (DIC), it is necessary to block the coagulation cascade through the use of anticoagulants, such as heparin, coumarin, derivatives of coumarin, indandione derivatives, or other agents. For example, a heparin treatment or an extracorporeal treatment with citrate ion (U.S. Pat. No. 4,500,309) may be used in dialysis to prevent coagulation in the course of treatment. Heparin is also used in preventing deep vein thrombosis in patients undergoing surgery. Treatment with low doses of heparin may, however, cause heavy bleeding. Furthermore, because heparin has a half-life of approximately 80 minutes, it is rapidly cleared from the blood. Because heparin acts as a cofactor for antithrombin III (AT III), and antithrombin III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

In addition to the anticoagulants briefly described above, there are a variety of compositions disclosed within the art which are alleged to have anticoagulant activity. One such composition is disclosed by Reutelingsperger et al. (*Eur. J. Biochem.* 151: 625–629, 1985), who isolated a 32,000 dalton polypeptide from human umbilical cord arteries. Another composition is disclosed by Warn-Cramer et al. (*Circulation* Suppl, part 2, 74: 2–408ii, Abstract #1630, 1986). They detected a factor VIIa inhibitor of an apparent molecular weight of 34,500 in plasma. In addition, Broze et al. (*Circulation* Suppl, part 2, 74: 2–409ii, Abstract #1634, 1986) studied the inhibition of tissue factor by serum. Their results suggest that barium-absorbed serum contains a moiety which inhibits the factor VIIa-Ca++-tissue factor complex. However, none of these compositions has been well characterized.

Consequently, there is still a need in the art for improved compositions having anticoagulant activity which do not produce the undesirable side effects associated with traditional anticoagulant compositions. The present invention fulfills this need, and further provides other related advantages.

DISCLOSURE OF THE INVENTION

Briefly stated, the present invention discloses novel proteins which have therapeutic potential as both anticoagulants and as anti-inflammatory agents. In addition, the present invention discloses the heretofore unrecognized use of lipocortins in reducing blood coagulation in warm-blooded animals.

In one aspect of the present invention, the novel proteins generally have the following properties: (a) they bind to phospholipids; (b) they inhibit phospholipase $A_2$; (c) they bind to anion-exchange chromatographic media; and (d) they exhibit anticoagulant activity. In addition, the proteins also exhibit anti-inflammatory activity.

In another aspect of the present invention, the proteins generally have the following properties: (a) they bind to phospholipids; (b) they inhibit phospholipase $A_2$; (c) they bind to anion-exchange chromatographic media; (d) they exhibit anticoagulant activity; and (e) they have a molecular weight of approximately 70,000 as determined by polyacrylamide gel electrophoresis. In addition, the proteins also exhibit anti-inflammatory activity.

In still another aspect of the present invention, the proteins generally have the following properties: (a) they bind to phospholipids; (b) they inhibit phospholipase $A_2$; (c) they do not bind to DEAE-Sepharose at pH 5 to pH 9 and a salt concentration above about 75 mM; and (d) they exhibit anticoagulant activity. In addition, the proteins also exhibit anti-inflammatory activity.

A related aspect of the present invention is directed toward a method for producing a representative protein exhibiting anticoagulant activity from a biological fluid. Suitable biological fluids include aqueous extracts of highly vascularized tissue and cell lysates. The method generally comprises (a) adding ammonium sulfate to the biological fluid to approximately 20% to 50% saturation to form a first precipitate and a supernatant; (b) adding ammonium sulfate to the supernatant to at least approximately 60% saturation to form a second precipitate; (c) isolating the second precipitate and dissolving the second precipitate in a suitable buffer to form a solution; (d) reducing the salt concentration of the solution such that the reduced solution can be fractionated by anion-exchange chromatography; (e) fractionating the reduced solution by anion-exchange chromatography to produce an adsorbed fraction and a non-adsorbed fraction. In one embodiment, the adsorbed fraction is further fractionated by gel filtration to produce an enriched fraction, subsequently reducing the salt concentration of the enriched fraction such that the reduced fraction can be fractionated by cation-exchange chromatography, and then further fractionating the reduced fraction by cation-exchange chromatography to separate the protein having anticoagulant activity from the reduced fraction. The method may also include, after the step of fractionating the reduced solution, concentrating the adsorbed fraction. It is preferred that buffers and other solutions used within the method contain a chelating agent, such as EDTA.

Within a related embodiment, the non-adsorbed fraction is further fractionated by gel filtration to produce an enriched fraction, the salt concentration of the enriched fraction is subsequently reduced such that the reduced fraction can be fractionated by cation-exchange chromatography, and then the reduced fraction is further fractionated by cation-exchange chromatography to separate the protein having anticoagulant activity from the reduced fraction. The method may also include, after the step of fractionating the reduced solution, concentrating the non-adsorbed fraction.

Pharmaceutical compositions comprising an effective amount of one of the proteins described herein in combination with a physiologically acceptable carrier or diluent are also disclosed. Suitable carriers or diluents include sterile water and physiological saline. The pharmaceutical compositions are particularly useful in reducing blood coagulation in warm-blooded animals as well as reducing inflammation in warm-blooded animals.

In addition, as noted above, the present invention discloses that lipocortins, including lipocortin I and lipocortin II, may be used within a method for reducing blood coagulation in warm-blooded animals. The method generally comprises administering to a warm-blooded animal an effective amount of the lipocortin in combination with a physiologically acceptable carrier or diluent.

The present invention discloses purified DNA sequences encoding the proteins described above. Host cells transfected or transformed with an expression vector containing these DNA sequences are also disclosed.

Other aspects of the present invention will become evident upon reference to the following detailed description and attached drawings.

BRIEF DESCRIPTION OF THE DRAWINGS

FIG. 5 illustrates the amino acid sequences of PAP-I, lipocortin-I and the partial amino acid sequences of PAP-II, PAP-III and PAP-IV. Regions of amino acid identity are boxed. Tentatively-identified methionine residues are designated by a lower-case m. Unidentified residues are designated by an upper-case X.

FIG. 8 shows the cDNA sequence encoding PAP-I and the amino acid sequence deduced from the cDNA sequence. The amino-terminal methionine residue, designated (M), is removed from the mature protein after translation.

BEST MODE FOR CARRYING OUT THE INVENTION

Figure 1:
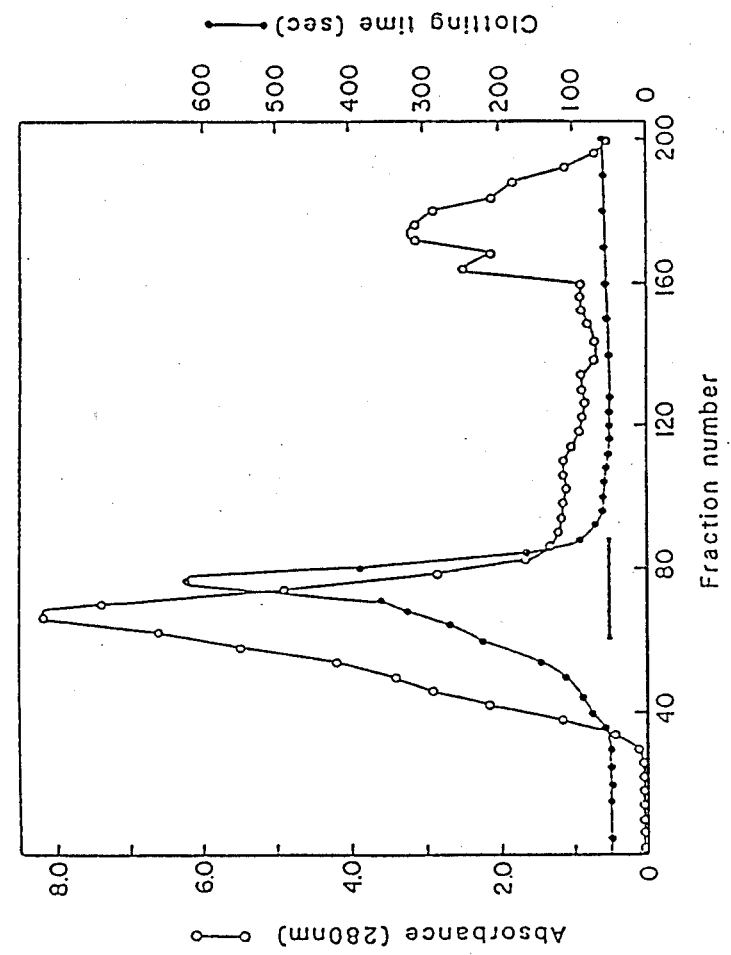
FIG. 1 illustrates an elution profile of a DEAE-Sepharose column. The bar indicates pooled fractions used for subsequent purification of two representative proteins of the present invention.

Prior to setting forth the invention, it may be helpful to an understanding thereof to define certain terms to be used hereinafter.

Anticoagulant activity: "Anticoagulant activity" is defined as the ability to inhibit blood coagulation. As previously noted, blood coagulation is a complex process involving the interaction of various elements, including enzymes, cofactors, ions and phospholipids. Compounds exhibiting anticoagulant activity may exert this activity by interfering with any of these elements. For example, heparin interferes with the action of factor Xa by accelerating the formation of complexes between antithrombin III, thrombin and factor Xa; while protein C, a blood protein, exerts its anticoagulant activity by inactivating factors Va and VIIIa. As used herein, "reducing blood coagulation" shall include reducing or preventing coagulation in vivo by any mechanism. Anticoagulant activity is assayed in an in vitro clotting assay, such as the kaolin-induced clotting assay or the thromboplastin-induced clotting assay. For the purposes of the present invention, a compound is said to exhibit anticoagulant activity when its addition to such an assay system results in delayed clotting, such as delayed fibrin generation.

Anti-inflammatory activity: Anti-inflammatory activity is the ability to interfere with the inflammatory process, thereby reducing or eliminating any or all of the symptoms of inflammation. According to current understanding, anti-inflammatory activity is typically the result of interference with the production of prostaglandins and/or leukotrienes, compounds which appear to be major physiological mediators of inflammation. A key step in the inflammation process is the generation of arachidonic acid from phospholipids by phospholipase $A_2$. Compounds which inhibit the action of phospholipase $A_2$, for example, by binding to phospholipids, will exhibit anti-inflammatory activity. For the purposes of the present invention, a compound will be recognized as exhibiting anti-inflammatory activity if it inhibits phospholipase $A_2$ or otherwise interferes with prostaglandin synthesis. Assay systems for anti-inflammatory activity are known in the art.

Biological fluid: A liquid containing cells, portions of cells or cell products. Biological fluids include, but are not limited to, tissue homogenates, tissue extracts, blood, plasma, serum, cell lysates and cell-conditioned culture media.

Phospholipid: The phospholipids are a class of compounds consisting of fatty acid molecules esterified to the first and second hydroxyl groups of glycerol, with the third hydroxyl group of the glycerol moiety esterified to phosphoric acid. Phospholipids occur in cell membranes and, as noted above, contribute to both blood coagulation and inflammation. For example, prothrombin and factor Xa bind to membrane phospholipids, resulting in the activation of prothrombin to thrombin. As used herein, the phrase "binds to phospholipid" shall mean binding to phospholipid vesicles prepared from rabbit brain cephalin (a mixture of neutral and acidic phospholipid) or a mixture of phosphatidylserine:phosphatidylcholine (molar ratio 20:80) in a standard assay system.

Phospholipase $A_2$: As noted above, phospholipase $A_2$ is an enzyme which cleaves certain phospholipids to release arachidonic acid, a precursor of prostaglandins and leukotrienes. As used herein, "inhibition of phospholipase $A_2$" refers specifically to inhibiting the production of arachidonic acid by phospholipase $A_2$, typically by binding to the phospholipid substrate.

Complementary DNA or cDNA: A DNA molecule or sequence which has been enzymatically synthesized from the sequences present in an mRNA template, or a clone of such a molecule.

DNA construct: A DNA molecule, or a clone of such a molecule, either single or double-stranded, which has been modified through human intervention to contain segments of DNA combined and juxtaposed in a manner which would not otherwise exist in nature.

One representative protein of the present invention has been found to have the following characteristics:
1. Molecular weight of 35,847 by amino acid composition.
2. Consists of approximately 319 amino acid residues.
3. Contains little or no carbohydrate.
4. Contains few or no disulfide bonds.
5. Binds to phospholipid.
6. Inhibits phospholipase $A_2$.
7. Binds to DEAE-Sepharose at pH 5 to pH 9 and a salt concentration below about 75 mM.
8. Isoelectric point of 4.8.

Another representative protein of the present invention has been found to have the following characteristics.

1. Molecular weight of ~70,000 by polyacrylamide gel electrophoresis.
2. Binds to phospholipid.
3. Inhibits phospholipase $A_2$.
4. Binds to DEAE-Sepharose at pH 5 to pH 9 and a salt concentration below about 75 mM.

Yet another group of representative proteins of the present invention have been found to have the following characteristics:
1. Binds to phospholipid.
2. Inhibits phospholipase $A_2$.
3. Does not bind to DEAE-Sepharose at pH 5 to pH 9 and a salt concentration above about 75 mM.
4. Molecular weight of 34,000–36,000 by polyacrylamide gel electrophoresis.

In addition, the proteins described herein also exhibit anticoagulant activity and anti-inflammatory activity.

The anticoagulant activity of the proteins described herein is believed to be due to their ability to bind to phospholipid. Accordingly, any activation step in the coagulation cascade that requires phospholipid may be inhibited by these proteins. Besides the activation of prothrombin by factor Xa, other phospholipid-dependent reactions, including the activation of factor X by complexes of factor IXa-phospholipid-$Ca^{++}$-factor VIIIa, or the activation of factor X by complexes of factor VIIa-$Ca^{++}$-tissue factor, would be expected to be inhibited by these proteins. In addition, the proteins of the present invention would be expected to inhibit the inactivation of factors VIIIa and Va by activated protein C. In contrast to other anticoagulant proteins which inactivate clotting factors, the proteins described herein inhibit the clotting factors without inactivating them. The use of these novel proteins may therefore be preferred in certain instances where it is desirable to maintain partial functioning of the coagulation system, thereby preventing severe bleeding from occurring.

At least some of the novel proteins described herein have been found to be highly homologous to the lipocortin family of proteins. The lipocortins have the following common features: (1) they have an inhibitory activity against phospholipase $A_2$ and inhibit the prostaglandin-leukotriene-mediated inflammatory response by blocking arachidonic acid synthesis; (2) their synthesis is stimulated by anti-inflammatory drugs, such as glucocorticoid and dexamethasone; and (3) they are the prime substrates of EGF receptor/tyrosine kinases or protein serine-threonine kinases.

Lipocortins, although they have different names, have been detected or isolated from human placenta, chicken embryo fibroblasts, columnar epithelial cells of intestine, guinea pig lung, and other cells. Molecular weights of lipocortins generally range between 34,000 and 38,000. The sequences of the only well-characterized lipocortins, lipocortin I and II, have been determined by cDNA sequencing. Lipocortin I and II were shown to contain over 50% sequence identity and to be composed of four repeated sequences. Each repeat has putative $Ca^{++}$-dependent phospholipid binding cortin I and lipocortin II may be prepared by the method of Huang et al. (*Cell* 46: 191–199, 1986) or by the use of recombinant DNA techniques as disclosed by Wallner et al. (*Nature* 320: 77–81, 1986) or Wallner et al. (WO 86/04094).

Sequence data for three representative proteins of the present invention (designated PAP-I, PAP-II and PAP-III) have revealed that these proteins, although tentatively regarded as members of the family of lipocortins, have several features distinct from any previously characterized lipocortin.

One of the primary differences between the PAP-1 protein described herein and lipocortins I and II is its capacity to bind to anion-exchange chromatographic media. Suitable media include DEAE-Sephadex, DEAE-cellulose, DEAE-Sepharose, QAE-Sephadex, and QAE-Sepharose. This difference reflects distinct structural characteristics, that is, differences in amino acid sequences. The capacity to bind in this manner requires either an overall negative charge or exposed areas of negative charge capable of participating in binding. Further, in contrast to the PAP-I protein described herein, lipocortin I may contain two disulfide bonds, because lipocortin I contains four cysteinyl residues as determined by cDNA sequencing.

Given the anticoagulant activity and anti-inflammatory activity of the proteins described herein, it is expected that these proteins will have therapeutic value as both anticoagulants and as anti-inflammatory agents.

The proteins of the present invention may be substituted for heparin or other traditional anticoagulants in the treatment of disseminated intravascular coagulation, deep vein thrombosis, or other conditions requiring anticoagulant therapy. It is preferable to administer the proteins of the present invention in an intravenous infusion in combination with a physiologically acceptable carrier or diluent. Therapeutic compositions may be formulated in accordance with routine procedures. Typically, such compositions will comprise a solution in sterile water or physiological saline. They may further comprise adjuvants, stabilizers or other diluents. A local anesthetic to relieve pain at the site of infusion may also be included.

Pharmaceutical compositions of the present invention for use as anticoagulants will preferably be provided in an infusion bottle labeled to indicate the level of anticoagulant activity present. The term "anticoagulant," as used herein, shall mean a compound which reduces the rate of blood coagulation as measured in a kaolin- or thromboplastin-induced clotting assay system.

As noted above, the novel proteins of the present invention are expected to have therapeutic value as anti-inflammatory agents. Inflammation involves the reaction of living tissue to infection or injury, normally resulting in healing and the restoration of tissue structure and function. Inflammation also involves a complex set of responses which neutralize and remove pathogens and lead to the repair of the affected area. Symptoms of inflammation include pain, heat, redness, swelling, and dysfunction. Vascular dilation occurs, together with exudation of fluid into the surrounding tissue.

Although inflammation may be generally regarded as a defensive mechanism, it can in some instances become a disease in itself. Such chronic conditions as arthritis are believed to result from uncontrolled chronic inflammation. In these cases, the inflammation reaction results in damage to tissue, which in turn results in increased inflammation. This process usually results in the formation of scar tissue. Such conditions as bursitis are also the result of inflammation, and often lead to severe pain and inhibition of function.

In instances where inflammation is chronic or otherwise unacceptable, reduction of inflammation by therapeutic means is indicated. Common anti-inflammatory agents include aspirin and glucocorticoids. These drugs appear to work by inhibiting the production of prostaglandins, which have been implicated as mediators of inflammation. It is believed that the glucocorticoids stimulate the production of lipocortins, which inhibit the action of phospholipase $A_2$ on phospholipids. The release of arachidonic acid from phospholipids by phospholipase $A_2$ is necessary for the synthesis of the prostaglandins. The novel proteins of the present invention bind to phospholipids, thereby blocking the production of arachidonic acid.

As used herein, the term "reducing inflammation" shall mean the inhibition, in vivo, of the inflammatory process. Although the physiological mechanisms of this process are not completely understood and are in some instances inferred from in vitro observations, reduced inflammation will result in a reduction in pain and swelling in the affected site, together with at least partial restoration of normal function.

The proteins described herein may be isolated from a variety of biological fluids, including aqueous extracts of highly vascularized human tissues, including placenta, brain, lung, heart and liver. A particularly preferred tissue source is human placenta. Typically, the tissue is chopped and the pieces are homogenized, for example, in a blender or mixer, in the presence of an appropriate buffer (pH 5 to 9, preferably containing a metal chelating agent). The homogenate is then filtered to remove tissue fragments, and the filtrate is centrifuged. The supernatant (aqueous extract) is then removed. Other biological fluids which may be used as sources of these proteins include cell lysates and culture media from cells which produce the protein(s), including cells containing DNA constructs encoding the protein(s).

The biological fluid is first fractionated by adding saturated ammonium sulfate solution or solid ammonium sulfate to approximately 20% to 50% of saturation, preferably about 40% of saturation, to form a first precipitate. The first precipitate is separated from the supernatant by centrifugation, and the supernatant is retained. Ammonium sulfate is added to the supernatant to at least about 60% of saturation, preferably about 80% of saturation, to form a second precipitate. The second precipitate is isolated by centrifugation and dissolved in a suitable buffer to form a solution. The buffer is preferably neutral or slightly basic (pH 7 to 9) and will contain about 10 to 75 mM salt (NaCl, KCl, etc.) and further containing about 0.5 mM-5 mM EDTA. A particularly preferred buffer in this regard is 50 mM Tris-HCl, pH 7.9, containing 50 mM NaCl and 1 mM EDTA. The salt concentration of the solution is then reduced, preferably by dialysis in the same buffer, such that the resulting material can be fractionated by anion-exchange chromatography. The material is applied to an anion-exchange chromatography column and fractionated by elution with a pH 7 to 9 buffer containing a salt gradient, preferably about 50–500 mM salt concentration, to produce adsorbed and non-adsorbed fractions. Preferred anionexchange chromatography media include DEAE-Sephadex, DEAE-cellulose and DEAE-Sepharose, with DEAE-Sepharose being particularly preferred. The resulting adsorbed and non-adsorbed fractions may then be concentrated to facilitate further purification. Preferred methods of concentration include ammonium sulfate precipitation and polyethylene glycol precipitation.

In one embodiment, the adsorbed fraction or the concentrated adsorbed fraction is then further fractionated by gel filtration to produce an enriched fraction.

Preferred gel filtration media include Sephadex G-75 and G-100. The enriched fractions are then treated to reduce the salt concentration, for example, by dialysis against a low pH buffer (pH 4.0 to 6.0), to permit further fractionation by cation-exchange chromatography. The resulting samples are fractionated by cation-exchange chromatography, preferably on a column of CM-Sephadex, SP-Sephadex, CM-cellulose or Mono-S, using a low pH buffer containing salt. Throughout the purification process, purification is monitored by assaying the various fractions for protein content (e.g., by absorbance at 280 nm or by polyacrylamide gel electrophoresis) and for anticoagulant activity (e.g., by standard kaolin- or thromboplastin- induced clotting assays). Fractions containing anticoagulant activity are pooled for further purification or use in compositions described herein. When isolating the protein from a source which is expected to contain phospholipid, it is preferred that all purification steps be carried out in the presence of a metal chelating agent, such as EDTA, preferably about 0.5-5 mM EDTA.

Two anticoagulant proteins were isolated from the adsorbed fraction from the anion-exchange chromatography. One of these proteins was designated PAP-I, and it was subsequently found to have a molecular weight of about 35,847 by amino acid composition. A second anticoagulant protein, with an apparent molecular weight of about 70,000, was also found in the adsorbed fraction. This protein did not react with an antibody against PAP-I.

In another embodiment, the non-adsorbed fraction from the anion-exchange chromatography is treated to reduce the salt concentration and fractionated by cation-exchange chromatography as described above. In some instances it may be preferable to enrich the material by gel filtration prior to the cation-exchange chromatography step. Fractions obtained by cation-exchange chromatography are further purified by gel filtration, for example on Sephadex G-75. Additional purification may be obtained using high performance liquid chromatography (HPLC). In this way three proteins were isolated from the non-adsorbed anion-exchange chromatography fraction. These proteins were designated PAP-II, PAP-III, and PAP-IV. Subsequent analysis showed that PAP-IV is a cleavage product of lipocortin II. These results indicate that at least five different proteins belonging to the lipocortin family are present in the EDTA extract of human placenta.

As noted above, the novel proteins of the present invention may also be produced by expressing cloned DNA sequences in recombinant cells. A cDNA sequence encoding one representative protein is disclosed herein. This cDNA was isolated from a human placenta cDNA expression library using an affinity-purified antibody to obtain a cDNA fragment, followed by re-screening of the library with the cloned cDNA fragment. Additional methods of cDNA cloning are also suitable; see, for example, Maniatis et al., eds. (*Molecular Cloning: A Laboratory Manual,* Cold Spring Harbor Laboratory, 1982).

For expression in recombinant host cells, the DNA sequence encoding the anticoagulant and anti-inflammatory protein is inserted into a suitable expression vector. Expression vectors useful in this regard will contain a transcription promoter operably linked to the DNA sequence to be expressed. It is preferred that the vectors also include a transcription terminator. Depending on the particular host cell selected, expression vectors may also contain an origin of replication, enhancer sequences, and other nucleotide sequences which regulate or enhance expression levels. Selectable markers, sequences which provide for the selection and maintenance of the vector in the host cell, may also be provided in the expression vector, although in some cases a selectable marker may be introduced into the host cell on a separate vector. Suitable expression vectors may be derived from plasmids or viruses, or may contain elements of both. Selection of the appropriate elements and construction of vectors is within the ordinary level of skill in the genetic engineering art.

A particularly preferred host cell is the yeast *Saccharomyces cerevisiae,* although other fungal cells, bacteria, and cells from multicellular organisms may also be used. *S. cerevisiae* may be cultured in relatively simple media, is inexpensive to culture, and can be made to produce large amounts of foreign protein cytoplasmically. This is particularly advantageous in the case of proteins which do not require disulfide bonding or glycosylation for their activity. To isolate a cytoplasmically produced protein, the cells are lysed, cell debris is removed, generally by centrifugation, and the resulting supernatant is fractionated by conventional chemical methods. Purification processes which may be employed include salt fractionation, ion-exchange chromatography, affinity chromatography, and high-performance liquid chromatography.

Techniques for transforming yeast are well known in the literature and have been described by, for example, Beggs (*Nature* 275: 104–108, 1978). Suitable expression vectors include YRp7 (Struhl et al., *Proc. Natl. Acad. Sci. USA* 76: 1035–1039, 1979), YEp13 (Broach et al., *Gene* 8: 121–133, 1979), pJDB248 and pJDB219 (Beggs, ibid.), and derivatives thereof. Such vectors will generally include a selectable marker. A defective selectable marker, such as the leu2-d gene of Beggs (ibid.) or the POT1 gene of Kawasaki and Bell (EP 171,142), is particularly preferred. Preferred promoters useful in yeast expression vectors include promoters from yeast glycolytic genes (Hitzeman et et al., *J. Biol. Chem.* 255: 12073–12080, 1980; Alber and Kawasaki, *J. Mol. Appl. Genet.* 1: 419–434, 1982; and Kawasaki, U.S. Pat. No. 4,599,311) or alcohol dehydrogenase genes, particularly the ADH2-4c promoter (also known as "ADR3-4c"; see Russell et al., Nature 304: 652–654, 1983). In addition, it is preferable to include a transcription termination signal, such as the TPI1 terminator, within the expression vector. For expression of proteins requiring disulfide bond formation, or to facilitate purification of the foreign protein, a signal sequence, preferably from a yeast gene encoding a secreted protein, may be joined to the coding sequence for the protein of interest. Preferred signal sequences include those of the alpha factor gene (Kurjan et al., U.S. Pat. No. 4,546,082) and the BAR1 gene (MacKay et al., U.S. Pat. No. 4,613,572).

Preferred prokaryotic host cells for use in carrying out the present invention are strains of the bacteria *Escherichia coli,* although Bacillus and other genera are also useful. Techniques for transforming these hosts and expressing foreign genes cloned in them are well known in the art (see, e.g., Maniatis et al., ibid.). Vectors used for expressing foreign genes in bacterial hosts will generally contain a selectable marker, such as a gene for antibiotic resistance, and a promoter which functions in the host cell. Appropriate promoters include the trp (Nichols and Yanofsky, *Meth. Enzymol.* 101: 155–164, 1983), lac (Casadaban et al., *J. Bacteriol.* 143: 971–980, 1980), and phage λ promoter systems (Queen, *J. Mol. Appl. Genet.* 2: 1–10, 1983). Plasmids useful for transforming bacteria include pBR322 (Bolivar et al., *Gene* 2: 95–113, 1977), the pUC plasmids (Messing, *Meth. Enzymol.* 101: 20–77, 1983; Vieira and Messing, *Gene* 19: 259–268, 1982), pCQV2 (Queen, *J. Mol. Appl. Genet.* 2: 1–10, 1983), and derivatives thereof. Plasmids may contain both viral and bacterial elements.

Higher eukaryotic cells (such as mammalian and insect cells) may also serve as suitable host cells within the present invention. Expression vectors for use in mammalian cells will comprise a promoter capable of directing the transcription of a cloned gene or cDNA introduced into a mammalian cell. Particularly preferred promoters are the mouse metallothionein-1 (MT-1) promoter (Palmiter et al., *Science* 222: 809–814, 1983), or the major late promoter of adenovirus 2. Also included in such expression vectors is a polyadenylation signal, located downstream of the DNA sequence insertion site. The polyadenylation signal may be that of the cloned gene, or may be derived from a heterologous gene.

Cloned DNA sequences may then be introduced into cultured mammalian cells by, for example, calcium phosphate-mediated transfection (Wigler et al., *Cell* 14: 725, 1978; Corsaro and Pearson, *Somat. Cell Genet.* 7: 603, 1981; Graham and Van der Eb, *Virol.* 52: 456, 1973) or electroporation (Neumann et al., *EMBO J.* 1: 841–845, 1982).

A small fraction of the cells integrate the DNA into the genome of the host cell or maintain the DNA in non-chromosomal nuclear structures. In order to identify these integrants, a gene that confers a selectable phenotype (a selectable marker) is generally introduced into the cells along with the gene of interest. Preferred selectable markers include genes that confer resistance to drugs, such as neomycin, hygromycin, and methotrexate. Selectable markers may be introduced into the cell on a separate expression vector at the same time as the gene of interest, or they may be introduced on the same expression vector.

The copy number of the integrated gene sequence may be increased through amplification by using certain selectable markers (e.g., dihydrofolate reductase, which confers resistance to methotrexate). The selectable marker is introduced into the cells along with the gene of interest, and drug selection pressure is applied. The drug concentration is then increased in a stepwise manner, with selection of resistant cells at each step. By selecting for increased copy number of cloned sequences, expression levels may be substantially elevated.

The selected host cells are grown in an appropriate culture medium, and the protein may be isolated as described above.

By way of clarification, the terminology used in the subject application corresponds to the terminology used in U.S. Ser. No. 059,355 as follows:

| 059,355 | Present Application |
|---|---|
| PAP-1 | PAP-I |
| PAP-2 | PAP-III |
| PAP-3 | PAP-II |
| PAP-4 | Unnamed 70 kd protein |
| — | PAP-IV/Lipocortin-II |

The following examples are offered by way of illustration and not by way of limitation.

Example 1

Anticoagulant Assay Method

Reagents: The complete content of one vial of rabbit brain cephalin (Sigma) was uniformly suspended in 100 ml of saline and used as a source of phospholipid. Equal volumes of phospholipid suspension and 0.033 M $CaCl_2$ were mixed before assay. Acid-washed kaolin (Fischer) was suspended in saline at 50 mg/ml.

Assay Procedure: Twenty μl of pooled normal human plasma, 20 μl of kaolin, and 10 μl of test sample were incubated for 10 minutes at 37° C., then 40 μl of $CaCl_2$-phospholipid mixture was added and clotting time was determined.

EXAMPLE 2

Preparation and Characterization of PAP-I

A: Purification

A fresh human placenta was obtained from a local hospital and the umbilical cord and amniotic membrane were removed. An aqueous extract was prepared from the placenta by first cutting it into small pieces with a meat chopper and then soaking it in 2 liters of cold 50 mM Tris-HCl buffer, pH 7.9, containing 50 mM NaCl and 1 mM EDTA (buffer A) to remove the blood. The buffer was drained and the washing was repeated twice with the same volume of buffer. The placenta was then transferred to a Waring blender and homogenized for 1 minute with 1 liter of cold buffer A containing 5 mM EDTA and 5 mM benzamidine. The homogenate was filtered through a sheet of gauze. Tissue remaining on the gauze was put into the blender and homogenization was repeated with 1 liter of buffer. The resulting homogenate was then filtered, and the two filtrates were combined.

Solid ammonium sulfate was added to the combined filtrates to 40% of saturation. The precipitate was removed by centrifugation. Ammonium sulfate was further added to the supernatant to 80% of saturation, and the resulting precipitate was collected by centrifugation. The 80% ammonium sulfate precipitate was then dissolved in 200 ml buffer A and dialyzed overnight against 8 liters of the same buffer with two changes of buffer to reduce the salt concentration.

The dialyzed sample was transferred to a 2-liter plastic beaker and stirred for 2 hours with 350 ml of DEAE-Sepharose gel that had been equilibrated with buffer A. After the DEAE-Sepharose gel was settled, the supernatant was decanted. The gel was then poured into a plastic column (4.5×23 cm) and the column was washed with 2 liters of the same buffer. Adsorbed proteins were then eluted with a linear gradient formed by 1 liter of buffer A and 1 liter of 500 mM NaCl in 50 mM Tris-HCl, pH 7.9 containing 1 mM EDTA. Fractions were assayed for anticoagulant activity by the method described in Example 1, and the active fractions associated with the descending edge of the first protein peak were pooled. A typical elution profile is shown in FIG. 1. The pooled enriched fractions are indicated by the bar.

Figure 2:
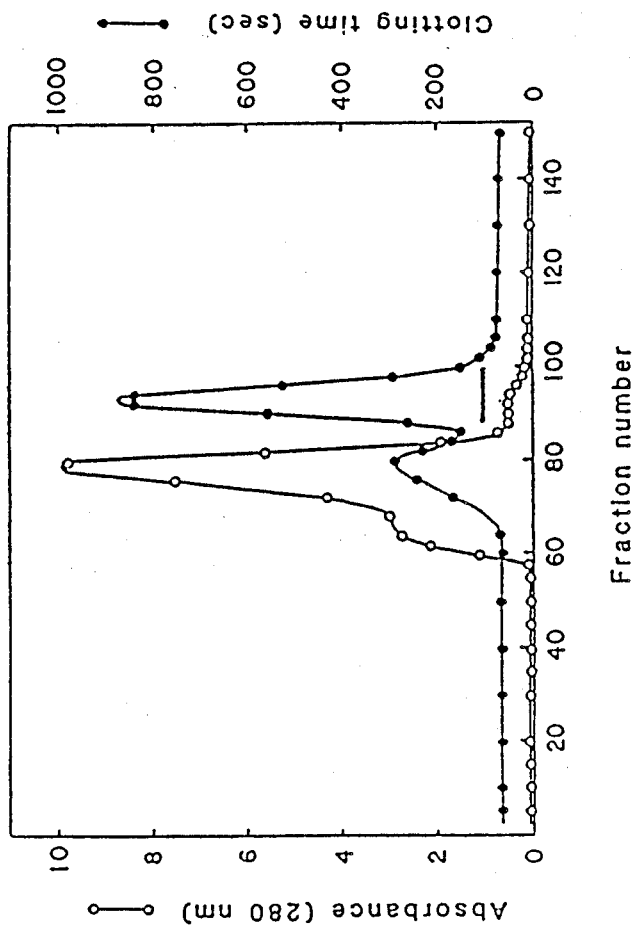
FIG. 2 illustrates an elution profile of a Sephadex G-75 gel filtration column. The bar indicates fractions pooled for subsequent purification steps.

To concentrate the enriched fraction, ammonium sulfate was added to 80% of saturation and the precipitate was collected by centrifugation. The precipitate was then dissolved in 50 ml of 50 mM Tris-HCl buffer, pH 7.9, containing 0.2 M NaCl and 1 mM EDTA (buffer B) and dialyzed for 2 hours against 2 liters of buffer B. The dialyzed sample was then applied to a column (5.5 x 100 cm) of Sephadex G-75 that had been equilibrated with buffer B. The column was eluted with buffer B at a flow rate of approximately 100 ml/h. The fractions which eluted after a major protein peak contained the anticoagulant activity. The enriched active fractions (indicated by the bar in FIG. 2) were pooled and dialyzed against 2 liters of 25 mM Na-acetate buffer, pH 5.2, containing 0.5 mM EDTA (acetate buffer) with two changes of buffer to reduce the salt concentration.

Figure 3:
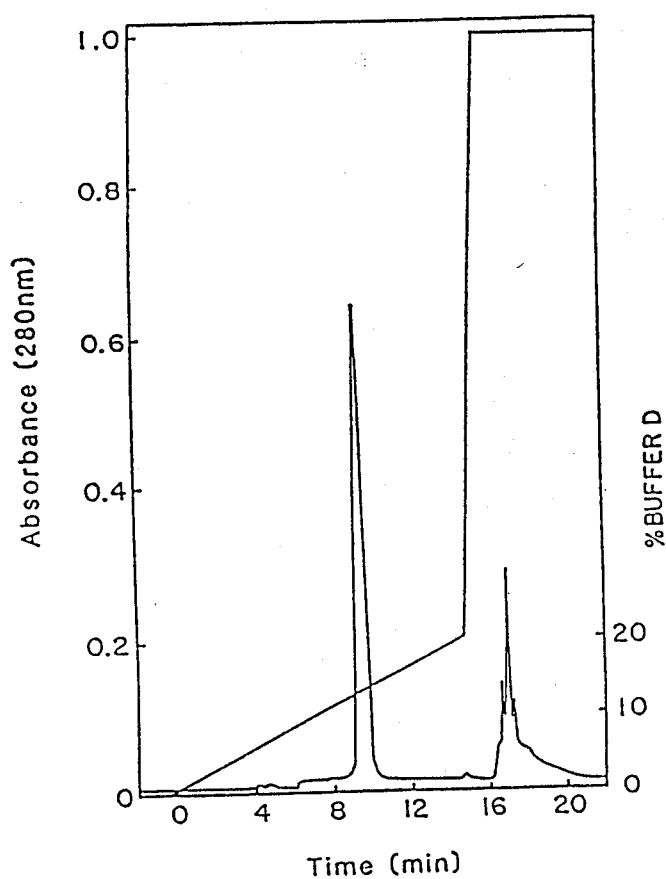
FIG. 3 illustrates chromatography of a representative PAP-I protein of the present invention on a Mono-S column. The protein is eluted from the column at approximately 12% buffer D.

The dialyzed sample was applied to a Mono-S column connected to a FPLC system (Pharmacia), and the adsorbed proteins were eluted with a linear gradient composed of buffer C (0.0 M NaCl in the acetate buffer) and buffer D (0.5 M NaCl in the acetate buffer). Elution was performed by a flow rate of 0.5 ml/min with a 0.67% increment of buffer D per minute. A major protein peak eluting at approximately 12% buffer D was collected (FIG. 3). This fraction contained homogeneous protein having anticoagulant activity. Approximately 20-25 mg of purified protein were obtained from one human placenta by this procedure.

B: Characterization

Figure 4:
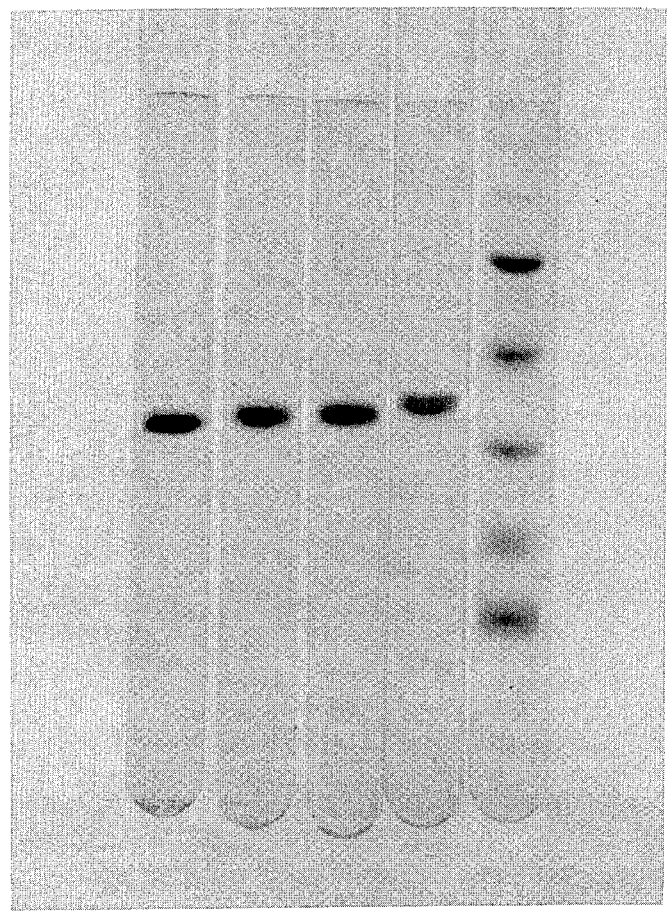
FIG. 4 illustrates SDS-polyacrylamide gel electrophoresis patterns of purified proteins having anticoagulant and anti-inflammatory activity. Lane 1, PAP-I; lane 2, PAP-II; lane 3, PAP-III; lane 4, PAP-IV; lane 5, molecular weight standards.

The purified PAP-I protein migrates as a single band (33,500 daltons) on SDS-polyacrylamide gel electrophoresis under reducing conditions (FIG. 4). The protein migrates as two bands of approximately 74,000 (40%) and 37,000 daltons (60%) on a non-reducing gel. The protein also gives a single band by disc gel electrophoresis.

The molecular weight of the purified PAP-I was estimated to be 36,500 by the Weber SDS polyacrylamide gel system (Weber and Osborn, *J. Biol. Chem.* 244: 4406, 1969).

The amino acid composition of a 24-hour acid hydrolysate of the protein was determined by a Waters picotag system and is shown in Table 1. The protein is composed of approximately 319 amino acid residues/molecule, plus one acetyl group, indicating the presence of a blocked amino acid residue at the amino terminus of the protein.

TABLE 1

| Amino Acid Composition of Protein (PAP-I) | |
|---|---|
| Amino Acids | Residues/mol |
| Asparagine | 6 |
| Aspartic acid | 25 |
| Glutamic acid | 29 |
| Glutamine | 12 |
| Serine | 21 |
| Glycine | 22 |
| Histidine | 3 |
| Arginine | 19 |
| Threonine | 23 |
| Alanine | 26 |
| Proline | 5 |
| Tyrosine | 12 |
| Valine | 16 |

TABLE 1-continued

| Amino Acid Composition of Protein (PAP-I) | |
|---|---|
| Amino Acids | Residues/mol |
| Methionine | 7 |
| Isoleucine | 18 |
| Leucine | 38 |
| Phenylalanine | 13 |
| Lysine | 22 |
| ½ cysteine | 1 |
| Tryptophan | 1 |
| Acetyl Group | 1 |
| TOTAL | 319 |

Shiff-base staining for carbohydrate on a SDS-polyacrylamide gel of the purified protein was negative, indicating that the protein contained little or no carbohydrate.

Purified PAP-I (4 mg) was digested for 24 hours at room temperature in 1 ml of 2% cyanogen bromide/70% formic acid and the resultant peptides were separated by a peptide reversed phase column (Pharmacia). The cyanogen bromide digest was dissolved in 1 ml of 0.1% aqueous trifluoroacetic acid (buffer E) and applied to the peptide reverse phase column. The peptides were eluted by a linear gradient composed of buffer E and buffer F (0.1% trifluoroacetic acid in 80% acetonitrile). Elution was performed by a flow rate of 1.5 ml/min with 2% increment/min of buffer F in buffer E. The peptide peaks that were detected by absorbance at 214 nm were collected manually. Amino acid sequences of four cyanogen bromide peptides, PAP-CNB-12, PAP-CNB-1, PAP-CNB-5 and PAP-CNB-15 were determined. The sequences of these four peptides revealed that this protein is composed of at least three repeated sequences which are homologous with three regions in lipocortin I, which is composed of four repeats.

A blocked peptide that originated from the NH$_2$-terminus was digested with lysine endopeptidase and the resulting peptides were separated by reversed phase C$_{18}$ HPLC column. One of the peptides of which the NH$_2$-terminus was blocked had a composition of one mole each of Glu, Gly, Arg, Thr, Ala, Val and Leu. This composition agreed with the 5' end sequence of seven residues deduced from the cDNA sequence. Thus, the NH$_2$-terminal sequence of PAP-I was found to be acetyl-Ala-Gln-Val-Leu-Arg-Gly-Thr.

The sequences of the four peptides (CNB-1, CNB-5, CNB-12 and CNB-15) and the highest homology of PAP-CNB-12 and PAP-CNB-1 with human lipocortin I are shown in Table 2. The sequence identity of PAP-CNB-12 and PAP-CNB-1 with the homologous regions of lipocortin I (residues 129-161 and 288-299, respectively) is over 50%. These regions of lipocortin are putative binding sites for phospholipid vesicles. Highly homologous sequences are also present in lipocortin II. These sequence data indicate that PAP-I is a member of the family of lipocortins. It should be noted that PAP-I is 27 amino acids shorter than lipocortin I at the NH$_2$-terminal end.

TABLE 2

|  | 130　　　　　　　　　　150 |
|---|---|
| Lipocortin-I | KGLGTDEDTLIEILASRTNKEIRDINRVYREEL |
| PAP-CNB-12 | KPSRLYDAYELKHALKGAGTNEKVLTEIIASRTPEELRAIK |
|  | QVYEEEYGSSLEDDVV(G)DT(S)(G)YY |

TABLE 2-continued

|  | 290 | 300 |
|---|---|---|
| Lipocortin-I | KGVGTRHKALIRIM | |
| PAP-CNB-1 | KGAGTDDHTLIR | |
| PAP-CNB-5 | IKGDTSGDYKKALLLL(X)GEDD | |
| PAP-CNB-15 | KGLGTDEESILTLLTSRSNAQRQEISAAFKTLFGRDLLDD | |

Numbers on top of the sequences represent residue numbers of lipocortin-I from the $NH_2$-terminus. Residues that are identical in both of the proteins are underlined. Residues in parentheses were tentative or undetermined in these experiments. The complete sequence of PAP-I is shown in FIG. 5.

Amino acid residues are designated within Table 2 by single letter code as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine; (X) indicates any unknown residue.

The proteins described herein prolong both the intrinsic and extrinsic clotting times of human plasma. Kaolin-induced clotting activities were assayed by incubating 20 μl of kaolin (50 mg/10 ml), 20 μl of pooled normal human plasma and 10 μl of purified protein for 10 minutes at 37° C. Forty μl of $CaCl_2$-phospholipid was then added and clotting times were determined. Thromboplastin-induced clotting times were determined by the same procedure as the kaolin-induced assay except that 20 μl of human brain thromboplastin was used. The effects of the purified protein on partial thromboplastin and kaolin-induced clotting times are shown in Table 3. Addition of 300 ng of the purified protein increased the partial thromboplastin time from 70 to 160 seconds and addition of 100 ng of the protein increased the kaolin-induced clotting time from 77 to 130 seconds.

TABLE 3

Inhibitory effects of PAP-I on kaolin- and thromboplastin-induced clotting times

| Inhibitor (ng) | Clotting Times (seconds) | |
|---|---|---|
| | Kaolin | Thromboplastin-Induced |
| 0 | 77 | 70 |
| 10 | 82 | 74 |
| 20 | 89 | 77 |
| 40 | 100 | 84 |
| 60 | 110 | 90 |
| 80 | 120 | 97 |
| 100 | 130 | 105 |
| 150 | — | 124 |
| 200 | — | 137 |
| 300 | — | 160 |

The proteins described herein also inhibit the activation of prothrombin in normal human plasma by a complex of factor Xa-phospholipid-$Ca^{++}$. Factor Xa (5 ng) and the purified PAP-1 protein (50 ng) were incubated for 3 minutes at 37° C. Normal human plasma (20 μl) and 40 μl of phospholipid/$CaCl_2$ were then added to this preincubation mixture and the clotting time was determined. The clotting time with the purified protein was over 300 seconds, while the clotting time of a control sample without the anticoagulant protein was 43 seconds.

The purified PAP-I protein was shown to readily bind to phospholipid vesicles. Binding of PAP-I to phospholipid vesicles was measured by gel filtration of a PAP-1/phospholipid mixture. Phospholipid vesicles were prepared as follows: 0.4 mg of egg yolk phosphatidyl choline (PC) and 0.1 mg of bovine brain phosphatidyl serine (PS) in chloroform were mixed in a test tube, and the organic solvent was evaporated under $N_2$ gas. The dried lipid was suspended in 0.5 mL of 50 mM Tris, pH 7.4, containing 0.15 M NaCl, and the suspension was sonicated twice for 15 seconds (s). A complete binding mixture contained in 220 μL of buffer A 0.1 mg of phospholipid vesicles, 5 μg of $^{125}$I-PAP (total $2.5 \times 10^5$ cmp), BSA (1 mg/mL), and 5 mM $CaCl_2$. This mixture was applied to a column (0.7×14 cm) of Sepharose 4B that had been equilibrated with 50 mM Tris-HCl, pH 8.9, containing 50 mM NaCl, and the column was run with the same buffer. The eluate was collected in 0.5 ml fractions and the radioactivity was detected in the void volume fraction (tubes 5 and 6), indicating the binding of the anticoagulant to phospholipid vesicles. In the absence of phospholipid or $CaCl_2$ in the reaction mixture, the radioactivity was found in the later fractions (tubes 9 to 11). Maximum binding requires the presence of calcium ions in the reaction mixture.

PAP-I does not inhibit amidase activity of thrombin or factor Xa, nor does it bind to purified factor Xa. The amidase activities of factor Xa and thrombin were measured with Boc-Ile-Glu-Gly-Arg-MCA (methylcoumarin) and Boc-Val-Pro-Arg-MCA, respectively. Five ng of factor Xa or thrombin were incubated with 0.5 mM of the substrates in the presence or absence of 0.1 μg of PAP-I. The amidase activity was determined by the increase of fluorescence (emission 380 nm, excitation 460 nm). PAP-I had no effect on the amidase activity of either thrombin or factor Xa.

Four μg of factor Xa was mixed with 0.1 μg of PAP-I (total reaction volume of 20 μl) and applied to a gel filtration column of TSK 3000 (Toyo Soda) that had been equilibrated with 50 mM Tris-HCl, pH 7.9, containing 50 mM NaCl. Two peaks were found in the eluates. These elution positions corresponded to those of factor Xa and PAP-I. No protein peak was found at the position prior to factor Xa. This result shows the failure of the formation of a protein/protein complex between PAP-1 and factor Xa.

EXAMPLE 3

Preparation and Characterization of PAP-II, PAP-III and PAP-IV

The DEAE-Sepharose effluent fraction from Example 2 was used as a starting material for the preparation of PAP-II, -III and -IV. This fraction (2 liters) was dialyzed against 10 liters of 50 mM sodium acetate buffer, pH 5.2, with two changes of buffer. The dialyzate was then stirred for 30 minutes with 350 ml of CM-Sephadex that had been equilibrated with the acetate buffer. The resin was settled and the supernatant was decanted and discarded. The resin slurry was then poured into a plastic column (4.5 ×30 cm). After the column was washed with 2 liters of the acetate buffer, adsorbed proteins were eluted with a linear gradient system composed of 0.8 liter of 0 M and 0.8 liter of 0.5

M NaCl in the acetate buffer, and fractions were collected in 200 tubes. Every fifth tube was then assayed for anticoagulant activity as previously described. Two anticoagulant activity peaks emerged at salt concentrations of approximately 0.25 M and 0.42 M. The fractions of the first peak were pooled for PAP-II, and the second for PAP-III and -IV. Proteins in the pooled fractions were precipitated by adding ammonium sulfate to 80% of saturation.

The precipitates were dissolved in a minimum volume of 50 mM Tris-HCl buffer, pH 7.9, containing 0.2 M NaCl and 1 mM EDTA and were dialyzed briefly against the same buffer. The dialyzed samples (60 ml) were applied to a gel filtration column (5×150 cm) of Sephadex G-75, superfine (Pharmacia). Proteins were eluted with the same Tris-HCl buffer. In each case anticoagulant activity appeared at the descending edge of a major protein peak. The active fractions from each separation were pooled and concentrated by ammonium sulfate precipitation as described above. The concentrated samples were reapplied to the same columns. Both PAP-II and PAP-III/IV fractions gave similar elution profiles characterized by a major protein peak with a shoulder at the descending edge. The anticoagulant activities were associated with the shoulder peaks. The active fractions from each of the gel filtration columns were pooled and dialyzed against 25 mM sodium acetate buffer, pH 5.2, containing 0.5 mM EDTA.

Figure 6:
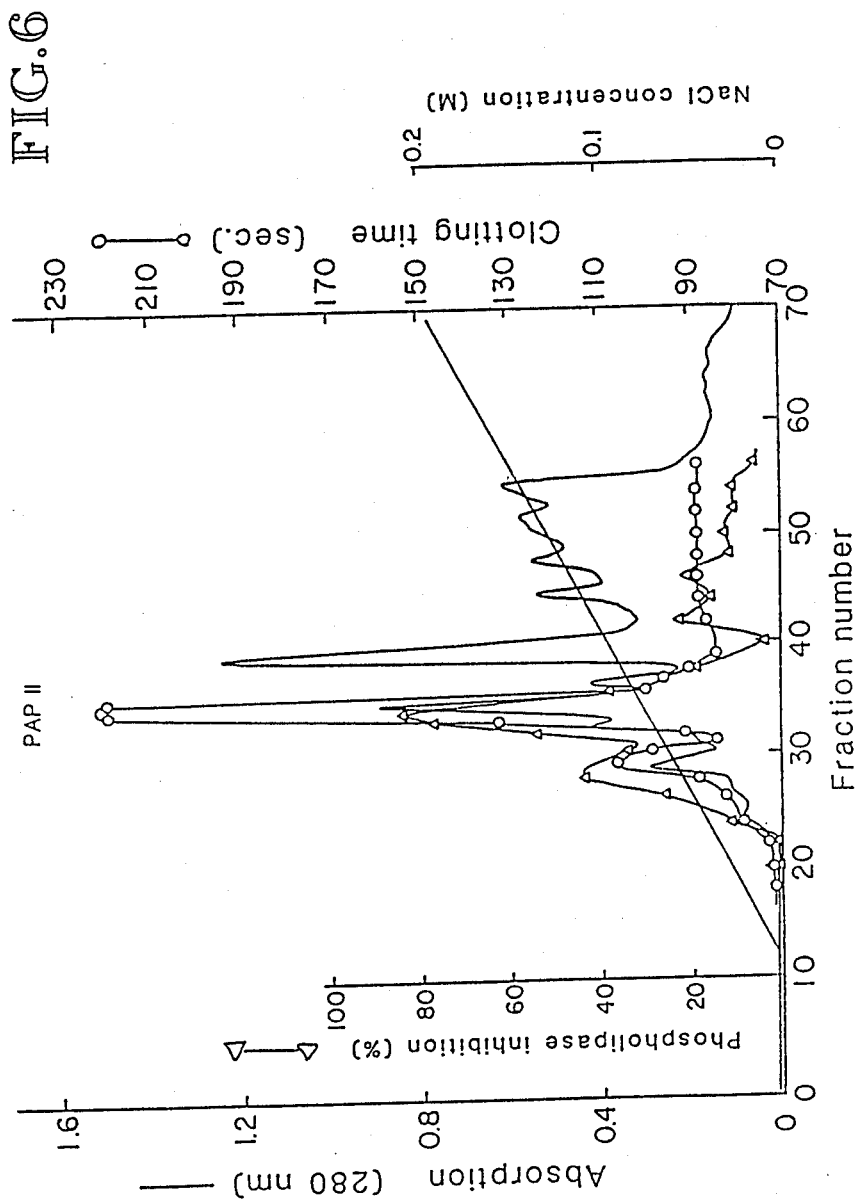
FIG. 6 illustrates the elution profile of PAP-II from a Mono S column.
Figure 7:
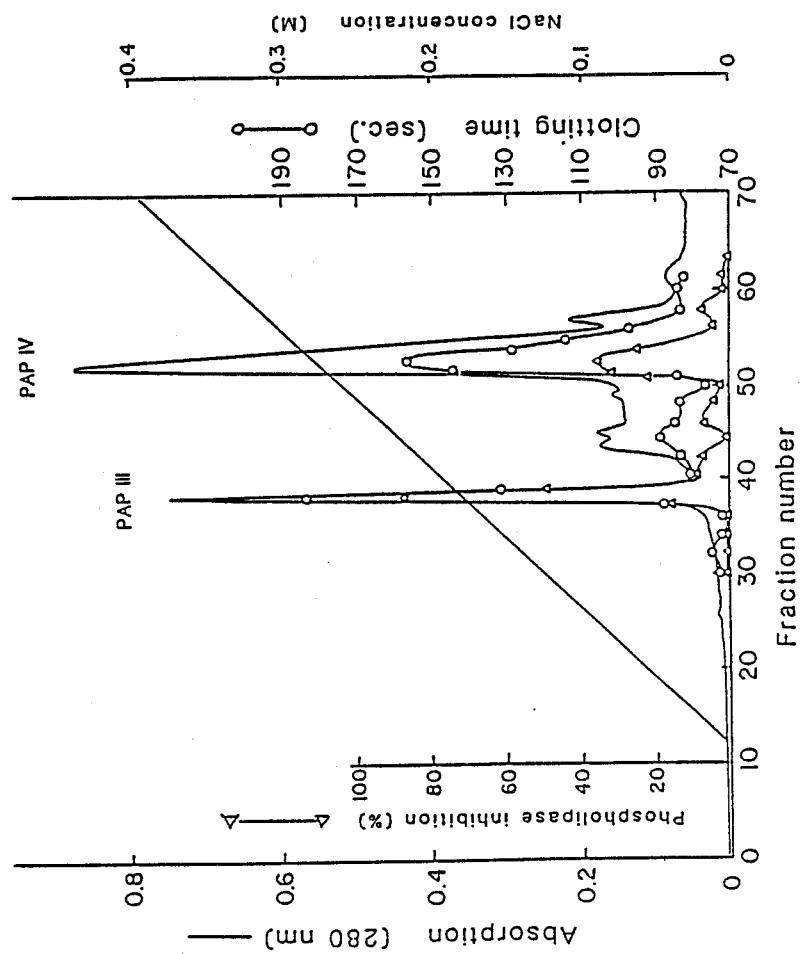
FIG. 7 illustrates the elution profile of PAP-III and PAP-IV from a Mono S column.

The dialyzed samples were then applied to a Mono S column connected to a Pharmacia FPLC system. Proteins were eluted by a linear NaCl gradient in 25 mM sodium acetate buffer, pH 5.2 containing 0.5 mM EDTA at a flow rate of 1 ml/min. Effluent was monitored by absorption at 280 nm and 0.5 ml fractions were collected. Every other fraction was assayed for anticoagulant activity and inhibition of phospholipase $A_2$ activity. The activities were found in two protein peaks from the PAP-II fraction at NaCl concentrations of 0.06 M and 0.08 M (FIG. 6). The protein associated with the second activity peak was PAP-II. Ouchterlony immunoprecipitation showed that the protein of the first activity peak was PAP-I. Active proteins were eluted from the PAP-III/IV fraction (FIG. 7) at salt concentrations of 0.17 M (PAP-III) and 0.27 M (PAP-IV). The yields from one placenta were 25 mg of PAP-I, 3 mg of PAP-II, 1 mg of PAP-III and 3 mg of PAP-IV, showing that PAP-I is by far the major protein of this family found in placenta.

SDS-polyacrylamide gel electrophoresis patterns of PAP-I, PAP-II, PAP-III and PAP-IV are shown in FIG. 4. All four of the proteins were purified to homogeneity. The estimated molecular weights of PAP-I, -II, -III, and -IV are 32,000, 34,000, 35,000 and 36,000, respectively. The molecular weight of PAP-I was determined to be 35,847 from the amino acid composition of the completed sequence, indicating a potential experimental error of about 4000 Da in the estimated molecular weights.

S-carboxymethylated PAP-II and PAP-III were digested with cyanogen bromide and the resulting fragments were separated by a HPLC system using a C3 reversed phase column. Amino acid sequence analyses were performed with six fragments from PAP-II, five fragments from PAP-III, and two fragments from PAP-IV. Approximately 180 residues from PAP-II, 130 residues from PAP-III, and 50 residues from PAP-IV were determined. Alignment of these sequences with PAP-I and lipocortin-1 is shown in FIG. 5. Amino-termini of PAP-I and PAP-III are blocked. Amino-termini of PAP-II and PAP-IV are not blocked.

It will be appreciated that other suitable proteins may be isolated by the above processes, or by variations of the above processes as previously described. For example, minor variations in protein structure may exist due to genetic polymorphisms or cell-mediated modifications of the proteins or their precursors. Furthermore, it will be evident to one skilled in the art that the amino acid sequence of a protein may be modified by genetic techniques to produce proteins with slightly altered biological activities.

EXAMPLE 4

Cloning of cDNA Encoding PAP-I

Figure 8:
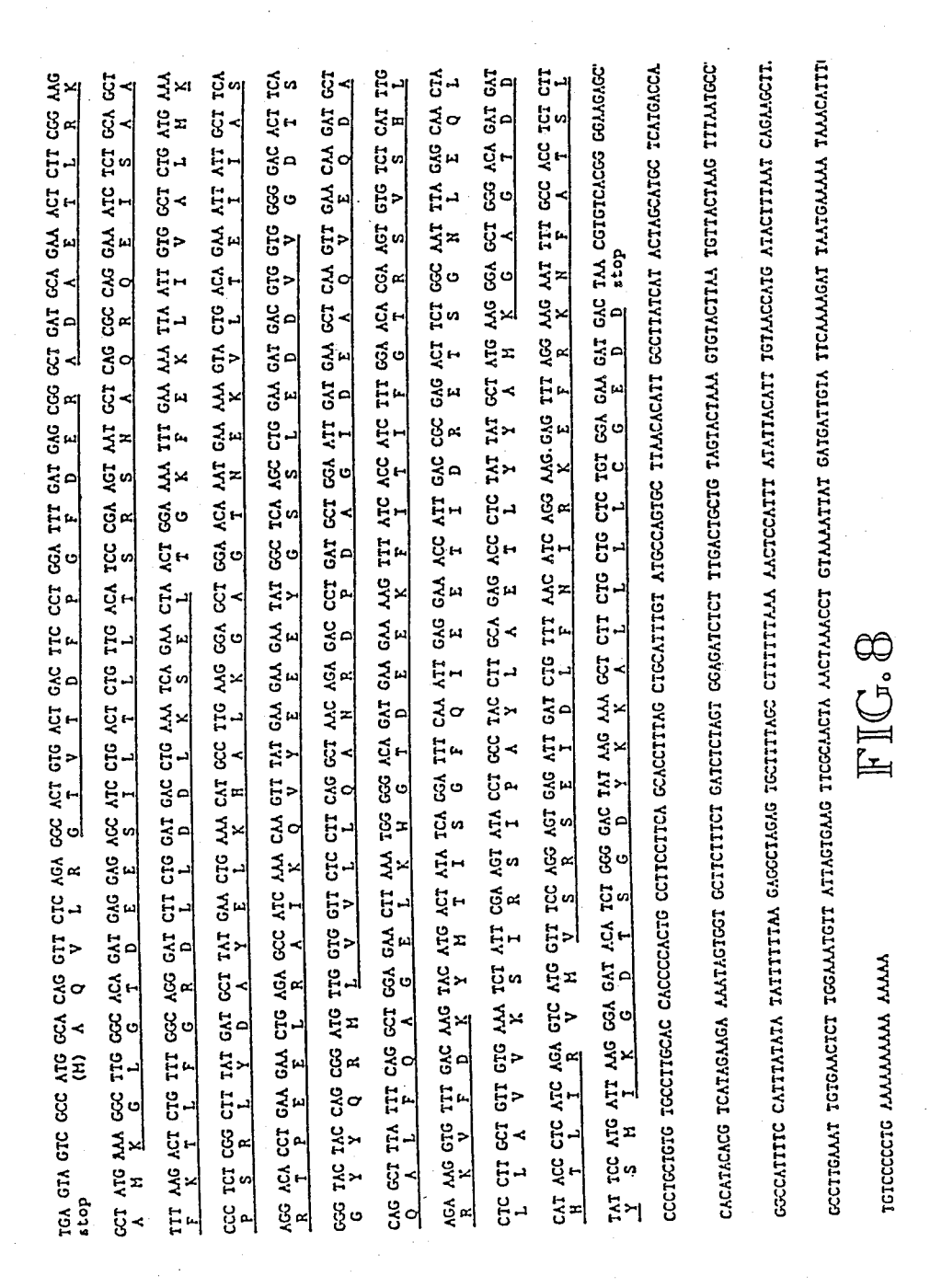

A human placenta cDNA library (Clontech) was screened using affinity-purified antibody against PAP-I according to the methods of Young and Davis (*Proc. Nat. Acad. Sci. USA* 80: 1194–1198, 1983) and Foster and Davie *Proc. Natl. Acad. Sci. USA* 81: 4766–4770, 1984). Twelve positive clones were obtained from $5\times10^5$ recombinants and were then plaque-purified. Sequence analysis of the largest clone (1.5 kb insert) showed that this clone contained an open reading frame sequence coding for PAP-I starting from residue 38 and extending to the 3' non-coding region containing the poly(A) tail. The original library was then re-screened using this clone as a hybridization probe. The probe was labeled by the method of Maniatis et al. (*Proc. Natl. Acad. Sci. USA* 72: 1184–1188, 1975). Filters were washed with 2 X SSC buffer (8.2 g of Na-citrate pH 7.0 and 17.5 g of NaCl/liter) containing 0.5% SDS at 60° C. for 1 hour. Twenty-four clones were then obtained and plaque-purified. Positive clones were subcloned into M13mp18 or M13mp19 for sequence analysis using the dideoxy-$^{35}$S method of Sanger et al. (*Proc. Natl. Acad. Sci. USA* 74: 5463–5467, 1977). The largest clone (1.7 kb insert) was found to contain a nearly full length cDNA and included an initiation Met residue at the 5' end followed by the entire mature protein, a stop codon, and a polyadenylation signal. The cDNA and deduced amino acid sequences (FIG. 8) agreed with the amino acid sequence obtained from the cyanogen bromide peptides. The cDNA sequence of PAP-I does not contain a leader peptide sequence, indicating that PAP-I is probably not constitutively secreted. The presence of Met at the 5' end by cDNA sequence analysis and the absence of this Met by protein sequence analysis showed that the Met residue is removed in a post-translational event and the newly formed $NH_2$-terminal Ala residue is blocked by acetylation. The $NH_2$-termini of lipocortin I and II are also blocked, but the nature of the blocking group is not known.

EXAMPLE 5

Expression of PAP-I in Yeast

For expression in yeast, the PAP-I cDNA was linked to the ADH2-4c promoter and the TPI1 terminator. This expression unit was inserted into several yeast expression vectors and the vectors were used to transform selected yeast strains.

Figure 9:
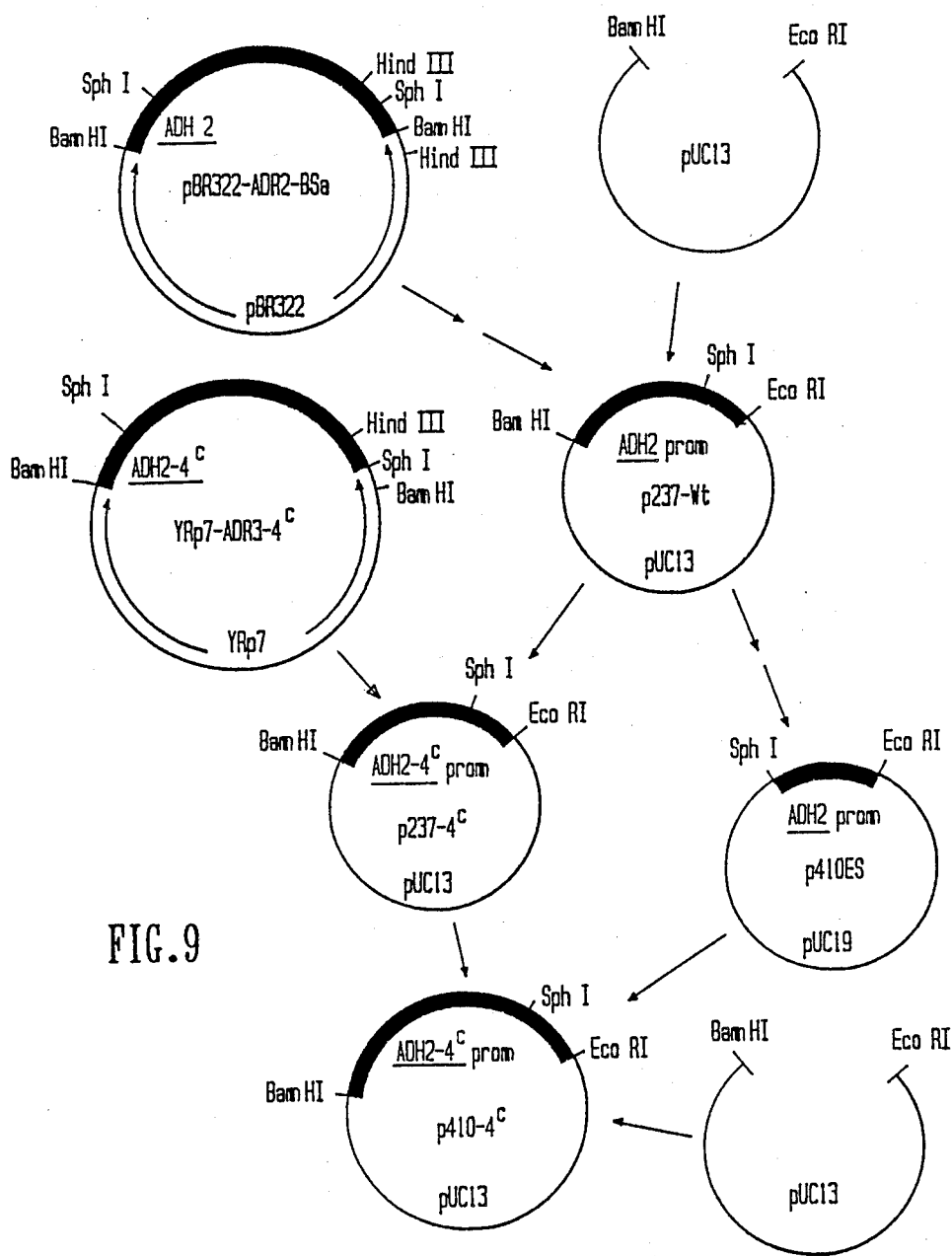
FIG. 9 illustrates the construction of an ADH2-4c promoter.

An ADH2-4c promoter was constructed by joining the downstream portion of the wild-type ADH2 (alcohol dehydrogenase II) promoter to the upstream portion of the ADH2-4c promoter described by Russell et al. (*Nature* 304: 652–654, 1983). The upstream sequences of the ADH2-4c promoter are responsible for its enhanced function. Construction of this promoter is illustrated in FIG. 9. The 2.2 kb Bam HI fragment containing the wild-type ADH2 structural gene and the 5' flanking sequences from pBR322-ADR2-BSa (Williamson et al., Cell 23: 605-614, 1981) was ligated with M13mp19 which had been linearized with Bam HI. The orientation of the insert was determined by restriction analysis. Oligonucleotide ZC237 (5' GCC AGT GAA TTC CAT TGT GTA TTA 3') was synthesized on an Applied Biosystems model 380A DNA synthesizer and purified by polyacrylamide gel electrophoresis. To isolate the promoter, site-specific in vitro mutagenesis (Zoller et al., DNA 3: 479–488, 1984) was done on the ADH2 insert in M13mp19 using ZC237 as the mutagenic primer and ZC87 (5' TCC CAG TCA CGA CGT 3') as the second primer. In positive clones, the oligonucleotide ZC237 looped out the structural portion of the ADH2 gene, fusing the 5' flanking sequence, including the translation start signal, with the Eco RI site of the M13mp19 polylinker. The replicative form of the mutagenized phage was made and cut with Bam HI and Eco RI to isolate the 1.2 kb promoter fragment. This fragment was ligated into pUC13 which had been linearized with Bam HI and Eco RI to generate plasmid p237-Wt. To change the p237-Wt promoter to the "promoter up" mutant ADH2-4c promoter, a 1.1 kb Bam HI-Sph I fragment from YRp7-ADR3-4c (Russell et al., ibid.) containing the alterations found to influence promoter function was subcloned into the vector fragment of p237-Wt which had been cut with Bam HI and Sph I. The resulting plasmid was designated p237-4c (FIG. 9).

The cloned ADH2-4c promoter was then modified by the addition of terminal restriction endonuclease cleavage sites. This was done by fusing the promoter to the codon for the first amino acid of the mature form of human alpha-1-antitrypsin (AAT) in the plasmid pAT-1. Plasmid pAT-1 comprises the expression unit of the ADH2 promoter from p237-Wt and an α-1-antitrypsin cDNA-TPI1 terminator sequence. These sequences were inserted into a portion of the vector pCPOT. (Plasmid pCPOT has been deposited with ATCC as an E. coli strain HB101 transformant and has been assigned accession number 39685. It comprises the entire 2 micron plasmid DNA, the leu2-d gene, pBR322 sequences and the *Schizosaccharomyces pombe* POT1gene.) Plasmid pCPOT was cut with Bam HI and Sal I to isolate the approximately 10 kb linear vector fragment. The 1.2 kb ADH2 promoter fragment was isolated from p237-WT as a Bam HI-Eco RI fragment and ligated with the 1.5 kb a-1-antitrypsin cDNA-TPI1 terminator fragment (Eco RI-Xho I) and the linearized pCPOT in a three-part ligation to yield a plasmid designated pAT-1.

Plasmid pAT-1 contained three extra amino acid codons between the ADH2 translation start codon and the first amino acid codon for the mature form of AAT. These three codons were removed by site-specific in vitro mutagenesis. plasmid pAT-1 was cut with Sph I and Bam HI to isolate the 190 bp ADH2 promoter fragment. This fragment was ligated into M13mp18 which had been linearized with Bam HI and Sph I. The resulting construction was subjected to in vitro mutagenesis using ZC411 (5'TAATACACAATGGAG-GATCCC3') as the mutagenic primer and ZC87 as the second primer to fuse the ADH2 translation start signal to the first codon of mature α-1-antitrypsin. Positive clones were confirmed by dideoxy sequencing from −170 bp from the ATG through the fusion point. For ease of manipulation, the 175 bp Sph I-Eco RI mutagenized promoter fragment was ligated into pUC19 linearized with Sph I and Eco RI. The resultant plasmid, comprising the 3' most 170 bp of the ADH2 promoter and the ADH2 translation start fused to the first amino acid of the mature form of AAT in vector pUC19, was designated p411.

To generate the complete ADH2-4c promoter fused to the codon for the first amino acid of mature AAT, the 5' most sequence of the ADH2-4c promoter, containing the alterations found by Russell et al. (supra.) to influence promoter function, was added to the promoter fragment present in plasmid p411. Plasmid p411 was digested with Sph I and Eco RI to isolate the 175 bp promoter fragment. Plasmid p237-4c was cut with Eco RI and Sph I to isolate the 3.71 kb fragment comprising pUC vector sequences and the 5' most promoter sequence that confers the "promoter-up" phenotype. The 175 bp promoter fragment from p411 was ligated into the p237-4c vector fragment. The resulting plasmid, containing the complete ADH2-4c promoter fused to the first amino acid codon of the mature AAT sequence, was designated p237-4cM.

The ADH2 promoter from plasmid pAT-1 was modified to create a "universal" promoter by removing the ADH2 translation start site and the pUC18 polylinker sequences found in pAT-1. Plasmid pAT-1 was cut with Sph I and Bam HI to isolate the 190 bp partial ADH2 promoter fragment. This fragment was ligated into M13mp18 linearized with Bam HI and Sph I. The resulting construction was subjected to in vitro mutagenesis using ZC410 (5'CGTAATACAGAATTCCCGGG3') as the mutagenic primer and ZC87 as the second primer to replace the ADH2 translation start signal and pUC18 polylinker sequences with a single Eco RI site fused to the M13mp18 polylinker at the Sma I site. Positive clones were confirmed by dideoxy sequencing through the fusion point. For ease of manipulation, the mutagenized partial ADH2 promoter fragment was subcloned as a 175 bp Sph I-Eco RI fragment into pUC19 which had been linearized with Sph I and Eco RI. The resulting plasmid, designated p410ES, contained the 3'-most 175 bp of the ADH2 promoter. The ADH2-4c promoter was then modified to contain this 3' sequence by combining the p410ES promoter fragment (Sph I-Eco RI) with the 1.1 kb Bam HI-Sph I ADH2-4c promoter fragment from p237-4c. The two promoter fragments were joined with Bam HI, Eco RI cut pUC13 in a three-part ligation. The resultant plasmid, confirmed by restriction analysis, contained the complete ADH2-4c promoter mutagenized at the 3' end to place an Eco RI site in place the translation start codon. This plasmid was designated p410-4c (FIG. 9).

The PAP-I cDNA was then joined to the ADH2-4c promoter. Plasmid pAPl.7, comprising the 1.7 kb cDNA in pUC18, was cut with Nco I and Bam HI and the linearized plasmid was isolated through two rounds of gel purification. The ADH2-4c promoter was functionally linked to the 5' end of the PAP-I cDNA through an adaptor having the following structure:

AATTCTACAC
GATGTGGTAC

Figure 10:
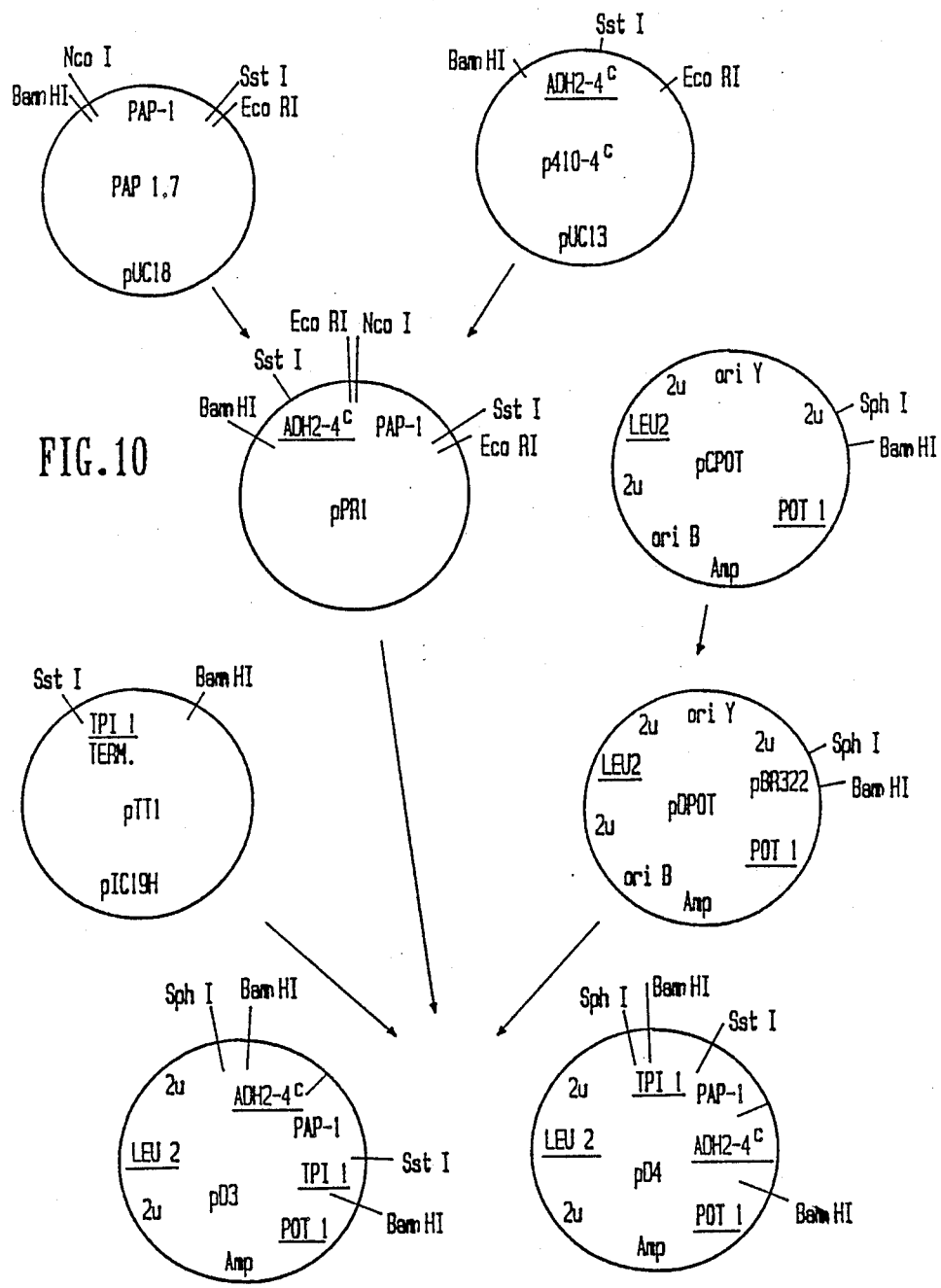
FIG. 10 illustrates the construction of expression vectors containing the PAP-I cDNA.

This was achieved by a three-part ligation using Nco I, Bam HI cut vector, the 1.2 kb Bam HI-Eco RI promoter fragment from p410-4c and the adaptor. The resultant plasmid was designed pPR1 (FIG. 10). The presence of the correct promoter fusion was confirmed by DNA sequencing.

Figure 11:
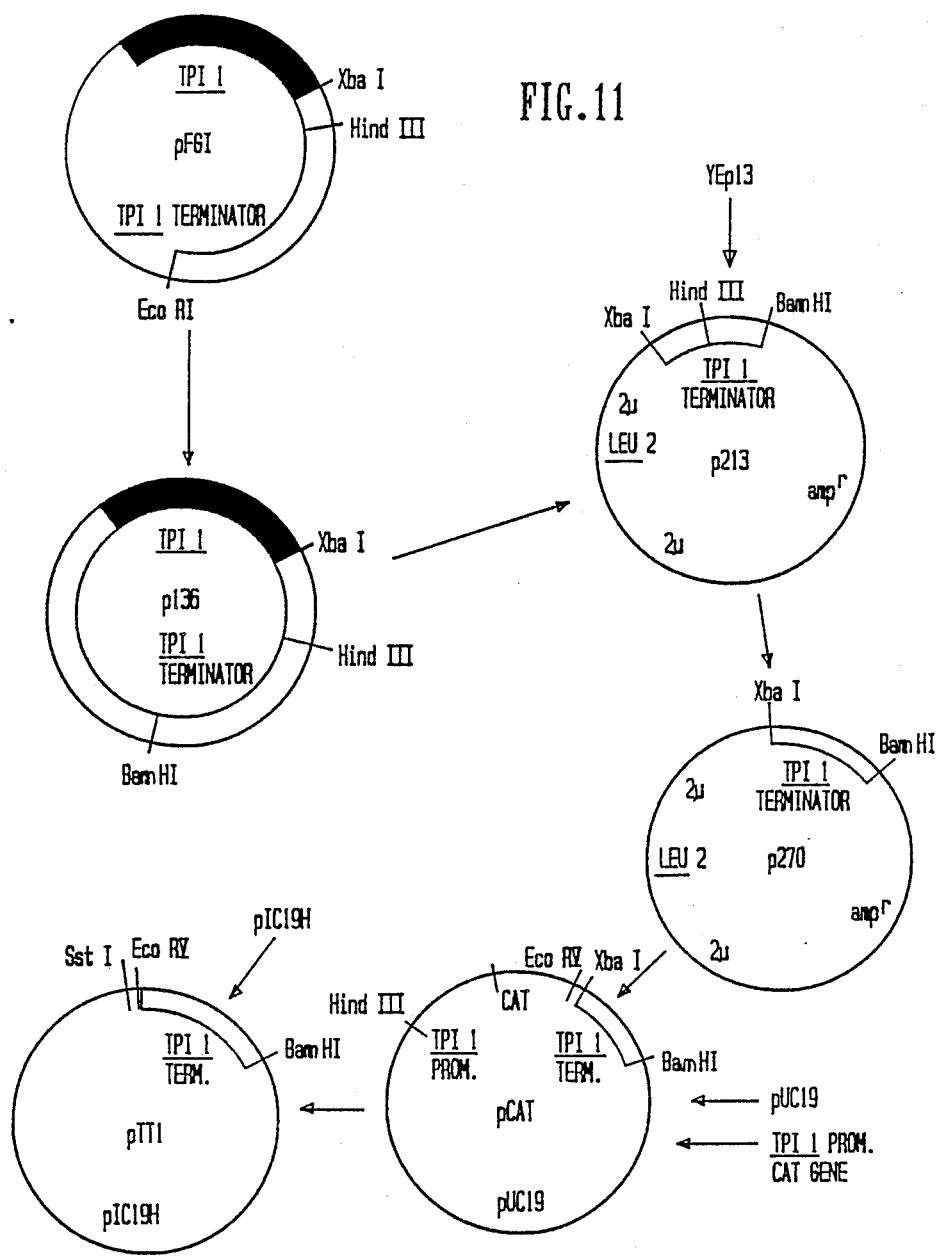
FIG. 11 illustrates the subcloning of the TPI1 terminator.

Expression vectors were then constructed as shown in FIGS. 10 and 11. Plasmid pCPOT was cleaved with Sph I and Bam HI to remove 750 bp of 2 micron and pBR322 sequences. The linearized vector was then joined to a 186 bp Sph I-Bam HI fragment derived from the pBR322 tetracycline resistance gene. The resulting plasmid, designated pDPOT (FIG. 10) was cut with Bam HI and treated with calf intestinal phosphatase. Plasmid pPR1 was digested completely with Bam HI and partially with Sst I and the ~2.1 kb promoter +PAP-I fragment was recovered. The yeast TPI1 terminator fragment was obtained from plasmid pFG1 (Alber and Kawasaki, *J. Mol. Appl. Genet.* 1: 419-434, 1982; see FIG. 11). It encompasses the region from the penultimate amino acid codon of the TPI1 gene to the Eco RI site approximately 700 base pairs downstream. A Bam HI site was substituted for this unique Eco RI site of pFGI by first cutting the plasmid with Eco RI, then blunting the ends with DNA polymerase I (Klenow fragment), adding synthetic Bam HI linkers (CGGATCCA), and re-ligating to produce plasmid p136. The TPI1 terminator was then excised from p136 as a Xba I-Bam HI fragment. This fragment was ligated into YEp13 (Broach et al., *Gene* 8: 121, 1979) which had been linearized with Xba I and Bam HI. The resulting plasmid is known as p213. The Hind III site was then removed from the TPI1 terminator region of p213 by digesting the plasmid with Hind III, blunting the resultant termini with DNA polymerase I (Klenow fragment), and recircularizing the linear molecule using T4 DNA ligase. The resulting plasmid was designated p270 (FIG. 11).

Alternatively, p270 may be constructed by digesting plasmid pM220 (deposited with American Type Culture Collection as an *E. coli* RR1 transformant, accession number 39853) with Xba I and Bam HI, purifying the TPI1 terminator fragment (~700 bp) and inserting this fragment into Xba I, Bam HI digested YEp13.

The TPI1 terminator was removed from plasmid p270 as a Xba I-Bam HI fragment. This fragment was cloned into pUC19 along with another fragment containing the TPI1 promoter fused to the CAT (chloramphenicol acetyl transferase) gene to obtain a TPI1 terminator fragment with an Eco RV end. The resultant plasmid was designated pCAT (FIG. 11). The TPI1 terminator was then cut from pCAT as an Eco RV-Bam HI fragment and cloned into pIC19H (Marsh et al., *Gene* 32: 481-486, 1984) which had been cut with the same enzymes, to obtain pTT1 (FIG. 11). Plasmid pTT1 was digested with Sst I and Bam HI and the ~800 bp TPI1 terminator fragment was recovered. The three fragments (Bam HI-cut pDPOT, Bam HI-Sst I promoter +PAP-I and Sst I-Bam HI terminator) were then joined (FIG. 10). Two different expression vectors with opposite expression unit orientations were obtained. These vectors were designated pD3 and pD4.

Plasmid pD4 was transformed into *S. cerevisiae* homozygous diploid strain ZM118 (a/α pep4::URA3 tpil::URA3 leu2=ura3 bar1). The transformants were grown in Medium B (2% Bacto Yeast Extract, 0.5% ammonium sulfate with 2% glucose as the carbon source) for 48 hours at 30° C.

The cultures were centrifuged to pellet the cells and the spent medium was discarded. The cells were pelleted and washed with distilled water. The washed pellets were frozen at −80° C. before being assayed.

Crude glass bead lysates were made of the frozen cell pellets. The washed cell pellets were thawed on ice and diluted in an equal volume of phosphate-buffered saline (PBS). Glass beads (450-500 um) were added to one half the total volume. The cells were lysed by vortexing the mixture at full speed for one minute, three times, with the samples cooled on ice between vortex bursts. Larger samples of 50 ml or more were treated in the same manner but lysed in a Bead Beater (Biospec Products, Bartlesville, Oklahoma) and cooled in an ethanol-dry ice bath between bursts. The liquid was removed from the tubes with a pasteur pipet and transferred to a microfuge tube. The glass beads were washed once in the original volume of PBS. The beads were vortexed one minute and the liquid was removed by pasteur pipet and pooled with the original lysate. The lysates were then centrifuged in an Eppendorf microfuge (Brinkmann, Westbury, N.Y.) at top speed for five minutes. The supernatants were carefully removed and assayed for anticoagulant activity essentially as described in Example 1. The assay demonstrated that clotting was inhibited by the cleared lysates.

Yeast-produced PAP-I was purified and the anticoagulant activity was compared to that of placental PAP-I. Approximately 900 g (wet weight) of transformed *S. cerevisiae* cells were lysed in a Bead Beater with three 1 minute bursts in PBS. The beads were washed with 100 ml PBS and the lysate was centrifuged in an HB4 rotor (Sorval) at 4° C. for 60 minutes at 10,000 rpm. The supernatant was removed. Ammonium sulfate was added to the supernatant to 40% of saturation, and the mixture was incubated at 4° C. for at least 1 hour. The mixture was then centrifuged as above and the pellet was discarded. The volume of the supernatant was noted, then ammonium sulfate was added to the supernatant to give a final saturation of 70%. This mixture was incubated at 4° C. for at least 1 hour, then centrifuged as described above. The supernatant was discarded. The 70% ammonium sulfate pellet was resuspended in PBS using 80% of the volume noted for the 40% ammonium sulfate supernatant. Polyethylene glycol 1000 was added to the solution at a concentration of 14% by weight. This mixture was incubated at 4° C. for at least 1 hour, then centrifuged and the pellet was discarded. The supernatant was dialyzed against 50 ml Tris HCl pH 7.9 containing 50 mM NaCl and 1 mM EDTA. The supernatant was then passed over a DEAE-Sepharose fast flow column (Pharmacia, Piscataway, N.J.) using a gel volume of approximately 1 ml per 25 mg of protein. The column was washed in 50 mM Tris HCl pH 7.9, 50 mM NaCl and 1 mM EDTA and eluted with a gradient of the same buffer and 50 mM Tris HCl, pH 7.9, containing 1 M NaCl and 1 mM EDTA. PAP-I eluted at approximately 0.2 M NaCl. Fractions from the DEAE-Sepharose column were assayed by gel electrophoresis. Peak fractions were precipitated by the addition of ammonium sulfate to 70% saturation. The mixtures were incubated at 4° C.for at least 1 hour, then centrifuged. The pellets were resuspended in 50 mM Tris, pH 7.9, containing 0.2 M NaCl and 1 mM EDTA, using a minimal volume of buffer. The resulting colutions were passed over a Sephacryl S-200 (Pharmacia) column. Fractions from the S-200 column were assayed by gel electrophoresis. Peak fractions were dialyzed against 10 mM sodium acetate, pH 5.2. The dialyzed fractions were passed over an S-Sepharose (Pharmacia) fast-flow column and washed in the same buffer. The column was eluted with a gradient of the same buffer and 10 mM sodium acetate, pH 5.2, plus 1 M NaCl containing 0.5 mM EDTA. To assay the yeast-produced PAP-I, 100 μl of purified protein was combined with 100 μl each of kaolin (acid washed; Fisher Scientific Co., Pittsburgh, PA; 5 mg/ml in IBS [0.05 M imidazole pH 7.35, 0.1 M NaCl, 0.02% NaN$_3$]) and human brain cephalin (diluted 1:250 in IBS). This mixture was combined with 100 μl normal human plasma (George King Biochemical, Overland Park, Kan.) and incubated for 6 minutes. CaCl$_2$ was added to 35 mM and the clotting time was measured. Control samples contained 100 μl IBS or purified placental PAP-I in place of the yeast-produced protein. Results are shown in
TABLE 4.

TABLE 4

| Protein | Concentration (ug/ml) | Clotting Time (seconds) |
|---|---|---|
| Yeast PAP-I | 0 | 45.0 |
| | 1 | 46.0 |
| | 2 | 49.0 |
| | 4.1 | 63.5 |
| | 8.25 | 97.4 |
| | 16.5 | 131.4 |
| | 33 | 242.8 |
| | 66 | >350 |
| Placental PAP-I | 0 | 45.3 |
| | 1.57 | 54.7 |
| | 3.13 | 65.4 |
| | 6.25 | 102.4 |
| | 12.5 | 155.0 |
| | 25.0 | 333.0 |

EXAMPLE 6:

Antithrombotic Activity of PAP-I

PAP-I was administered to rabbits to test its antithrombotic effect and overall effects on the general condition of the animals.

The antithrombotic effect of PAp-I was tested in a rabbit model essentially as described by Diness et al. (*Thromb. Haemostas* 55: 410-414, 1986). Briefly, the rabbits were anesthetized by an intravenous bolus injection of sodium pentobarbital via a catheter in a marginal ear vein. Anesthesia was maintained by additional injections of pentobarbital. Both facialis veins were exposed via an incision in the ventral part of the neck and a segment of about one cm close to the jugular vein was isolated between two clamps. The segment was flushed with Aethoxysklerol (5 mg/ml), thus producing endothelial damage. Five minutes later the segment was flushed with saline, the clamps were removed, and the blood was allowed to flow through the segment for one minute. Total stasis was then produced by a ligature at the proximal end of the segment. Thirty minutes after the injection of Aethoxysklerol, the veins were removed and inspected for the presence of thrombi. The thrombi, if any, were placed in preweighed vials and the wet weights were determined.

The test compound (0.5 ml of 1.5 mg/ml PAP-I in 50 mM Tris, 50 mM NaCl, pH 7.9) was given to two rabbits immediately after flushing the segment with Aethoxysklerol, i.e., before the clamps were removed. The test compound was injected via an intravenous catheter in the ear which was not used for administration of sodium pentobarbital. Two rabbits were given conventional heparin (0.5 mg/kg) and four rabbits were given saline as controls.

For registration of blood pressure, a PE-90 catheter was placed in the carotid artery and kept open by a slow infusion of saline. This catheter was also used for blood sampling in rabbits receiving PAP-I. Blood samples (1.8 ml of blood +0.2 ml of citrate) were taken before and 10, 25, 45, 60, 90 and 120 minutes after administration of PAP-I. The samples were centrifuged at 2000 x g for 10 minutes. Plasma of each sample was divided between two vials and frozen within 30 minutes after blood sampling.

Results are presented in Table 5. In control rabbits a thrombus was found in all veins (two thrombi per rabbit). The means and 95% confidence limits were calculated from log values, transferring data into normal distribution. Calculated from log values, the mean of the total weight of thrombi per rabbit in the control group was 20.2 mg and the 95% confidence limits (±2 SD) were 5.0–81.5 mg. In the two rabbits receiving PAP-I two small thrombi were found in one rabbit and only one small thrombus in the other. In both cases the total weight of thrombi per rabbit was below the 95% confidence limits of the control group. Conventional heparin (0.5 mg/kg) totally prevented thrombus formation in two rabbits.

Blood pressure was completely unaffected by the intravenous administration of PAP-I. For comparison, a decrease by about 20 mm Hg was seen for a short period after administration of 0.1 ml of sodium pentobarbital (5%) or even by manipulation of the ear when the syringe was placed in the catheter. Also, no change in respiration was noticed.

TABLE 5

| Test Preparation | Weight of Single Thrombi (mg) | Total Weight of Thrombi per Rabbit (mg) |
|---|---|---|
| Control | 10–10 | 2 |
| Control | 3.4–5.6 | 9.0 |
| Control | 7.4–11.4 | 18.8 |
| Control | 16.7–32.6 | 49.3 |
| PAP-I | 1.7–1.7 | 3.4* |
| PAP-I | 0–1.2 | 1.2 |
| Heparin | 0–0 | 0 |
| Heparin | 0–0 | 0 |

*One thrombus was not isolated, but the sizes of the two thrombi were approximately the same.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for producing a protein exhibiting anticoagulant activity, comprising:
   a. homogenizing highly vascularized tissue in the presence of a pH 5 to pH 9 buffer to obtain an aqueous homogenate;
   b. removing tissue fragment from said homogenate to produce an aqueous extract;
   c. adding ammonium sulfate to the extract to approximately 20% to 50% of saturation to form a first precipitate and supernatant;
   d. adding ammonium sulfate to the supernatant to at least approximately 60% of saturation to form a second precipitate;

e. isolating the second precipitate and dissolving said second precipitate in a suitable buffer to form a solution;

f. reducing the salt concentration of said solution such that said reduced solution can be separated by anion-exchange chromatography;

g. applying the solution obtained from step (f) to an anion-exchange chromatography column and collecting the fraction obtained which is not absorbed onto said column, to produce a non-absorbed fraction, h. fractionating said non-adsorbed fraction by gel filtration to produce an enriched fraction having anticoagulant activity;

i. reducing the salt concentration of said enriched fraction such that said reduced fraction can be fractionated by cation-exchange chromatography; and j. fractionating said reduced fraction by cation-exchange chromatography to separate the protein having anticoagulant activity from the reduced fraction.

2. The method of claim 1, including, after the step of fractionating the reduced solution, concentrating the non-adsorbed fraction.

3. The method of claim 1 wherein steps a through j are carried out in the presence of a metal chelating agent.

* * * * *

UNITED STATES PATENT AND TRADEMARK OFFICE
CERTIFICATE OF CORRECTION

PATENT NO. : 4,937,324
DATED : June 26, 1990
INVENTOR(S) : Kazuo Fujikawa, Meher H. Irani and Bruce L. A. Carter It is certified that error appears in the above-indentified patent and that said Letters Patent is hereby corrected as shown below:

Column 1, line 4, after the heading, "CHROMATOGRAPHIC PURIFICATION OF HUMAN PROTEINS HAVING ANTICOAGULANT AND ANTI-INFLAMMATORY ACTIVITY", and before the subtitle, " CROSS-REFERENCE TO RELATED APPLICATION", please insert the following sentence:

--This invention was made with government support under grant number HL 16919 awarded by the National Institutes of Health. The government has certain rights in the invention.--.

Signed and Sealed this

Twenty-first Day of November, 1995

Attest:

BRUCE LEHMAN

Attesting Officer

Commissioner of Patents and Trademarks